US 7,468,352 B1
(12) United States Patent
Leppla et al.

(10) Patent No.: US 7,468,352 B1
(45) Date of Patent: Dec. 23, 2008

(54) MUTATED ANTHRAX TOXIN PROTECTIVE ANTIGEN PROTEINS THAT SPECIFICALLY TARGET CELLS CONTAINING HIGH AMOUNTS OF CELL-SURFACE METALLOPROTEINASES OR PLASMINOGEN ACTIVATOR RECEPTORS

(75) Inventors: Stephen H. Leppla, Bethesda, MD (US); Shi-Hui Liu, Gaithersburg, MD (US); Sarah Netzel-Arnett, Gaithersburg, MD (US); Henning Birkedal-Hansen, Bethesda, MD (US); Thomas Bugge, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 113 days.

(21) Appl. No.: 10/088,952

(22) PCT Filed: Sep. 22, 2000

(86) PCT No.: PCT/US00/26192

§ 371 (c)(1),
(2), (4) Date: Mar. 22, 2002

(87) PCT Pub. No.: WO01/21656

PCT Pub. Date: Mar. 29, 2001

Related U.S. Application Data

(60) Provisional application No. 60/155,961, filed on Sep. 24, 1999.

(51) Int. Cl.
*A61K 38/00* (2006.01)

(52) U.S. Cl. .................................................. 514/12

(58) Field of Classification Search ............... 514/2, 514/12
See application file for complete search history.

(56) References Cited

U.S. PATENT DOCUMENTS

| 5,519,120 A | * | 5/1996 | Dano et al. | 530/388.22 |
| 5,677,274 A | * | 10/1997 | Leppla et al. | 514/2 |
| 5,817,771 A | * | 10/1998 | Bayley et al. | 530/391.7 |

OTHER PUBLICATIONS

Klimpel et al. (PNAS 1992; 89: 10277-10281).*
Coombs et al. (J. Biol. Chem. 1998; 273: 4323-4328).*
Liaw, L and Crawford, H.C., "Functions of the extracellular matrix and matrix degrading proteases during tumor progression" Braz. J. of Med. and Biol. Res. (1999) 32:805-812.
Mazar, A.P. and Jones, T.R., Abstract, XP-002131000, #146 "High-affinity, small cyclic peptide urokinase plasminogen activator receptor (uPAR)-targeting ligands localize reporter and therapeutic conjugates to the surfaces of tumor cells and stimulated endothelial cells," Angst. Phar., 1999.

* cited by examiner

*Primary Examiner*—Brandon J Fetterolf
(74) *Attorney, Agent, or Firm*—Townsend and Townsend and Crew LLP

(57) ABSTRACT

The present invention provides methods of specifically targeting compounds to cells overexpressing matrix metalloproteinases, plasminogen activators, or plasminogen activator receptors, by administering a compound and a mutant protective antigen protein comprising a matrix metalloproteinase or a plasminogen activator-recognized cleavage site in place of the native protective antigen furin-recognized cleavage site, wherein the mutant protective antigen is cleaved by a matrix metalloproteinase or a plasminogen activator overexpressed by the cell, thereby translocating into the cell a compound comprising a lethal factor polypeptide comprising a protective antigen binding site.

17 Claims, 17 Drawing Sheets

Fig. 1
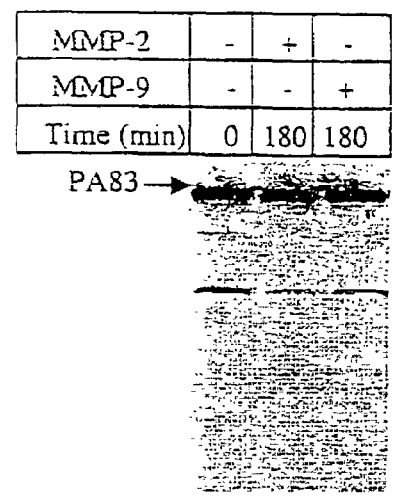
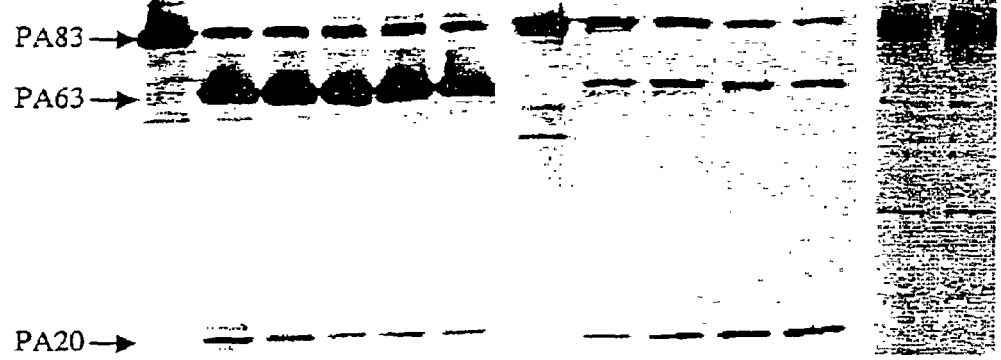
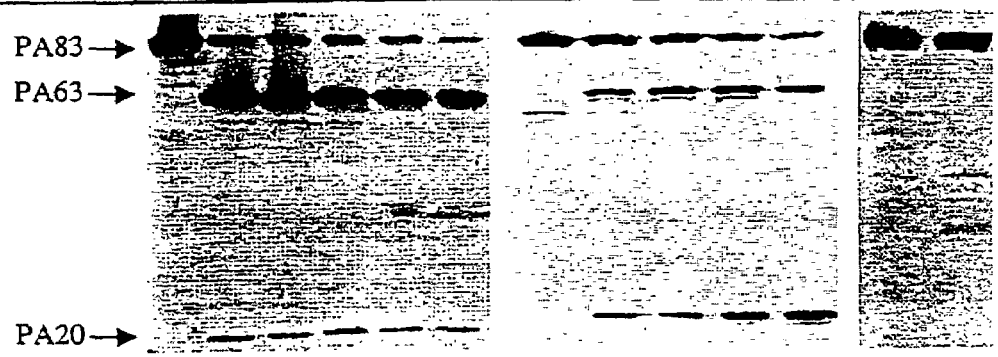

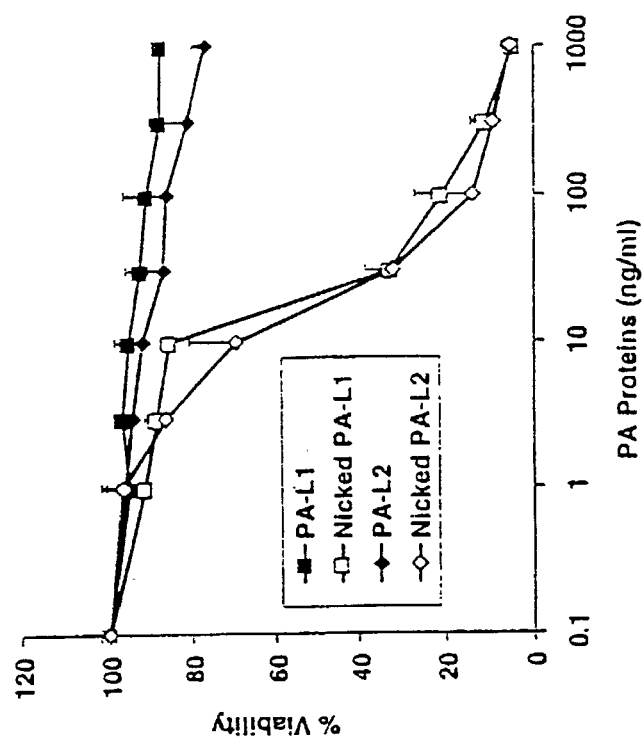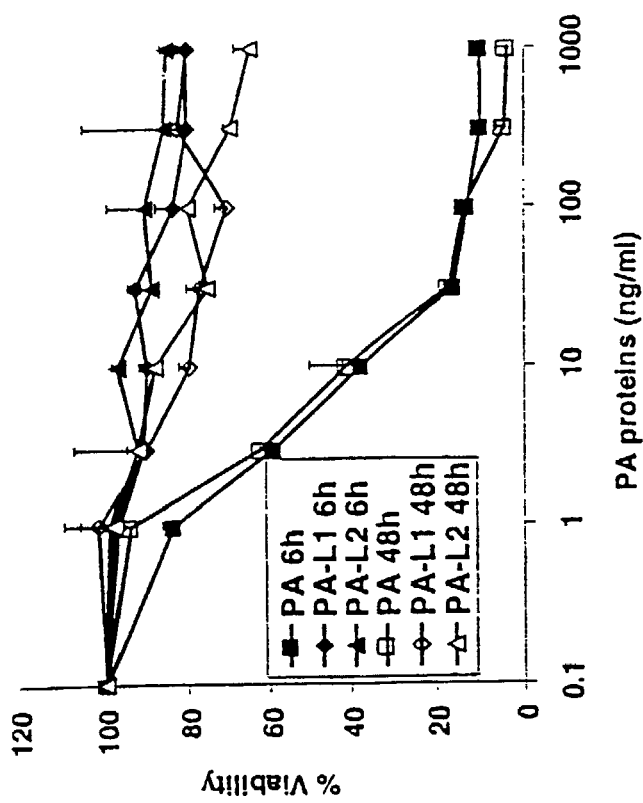
Fig. 3

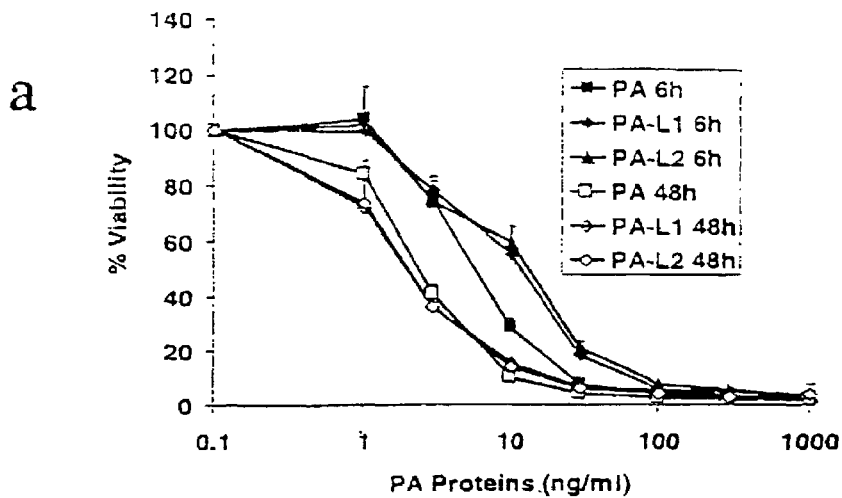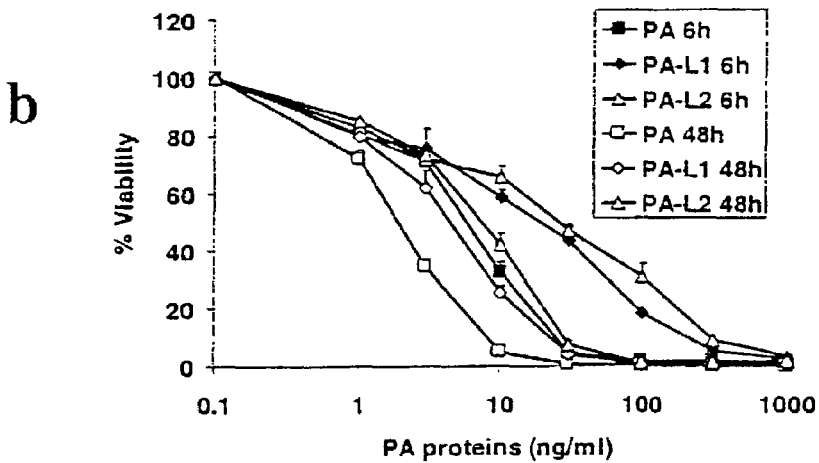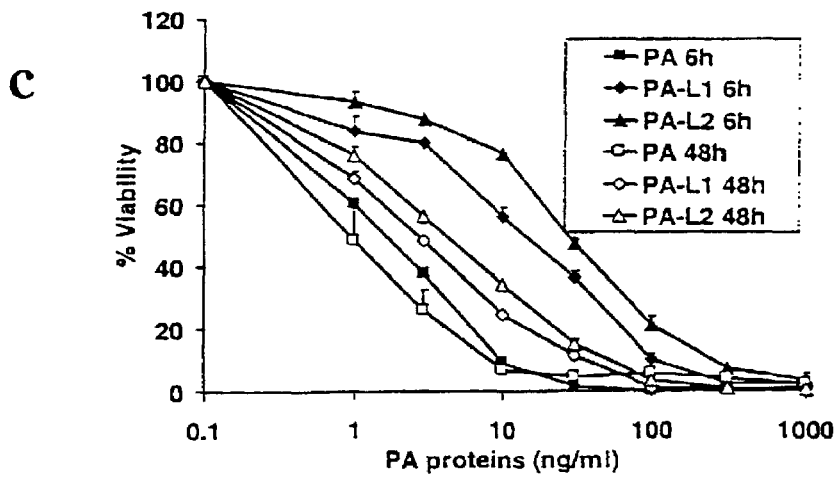
Fig. 4

Fig. 7
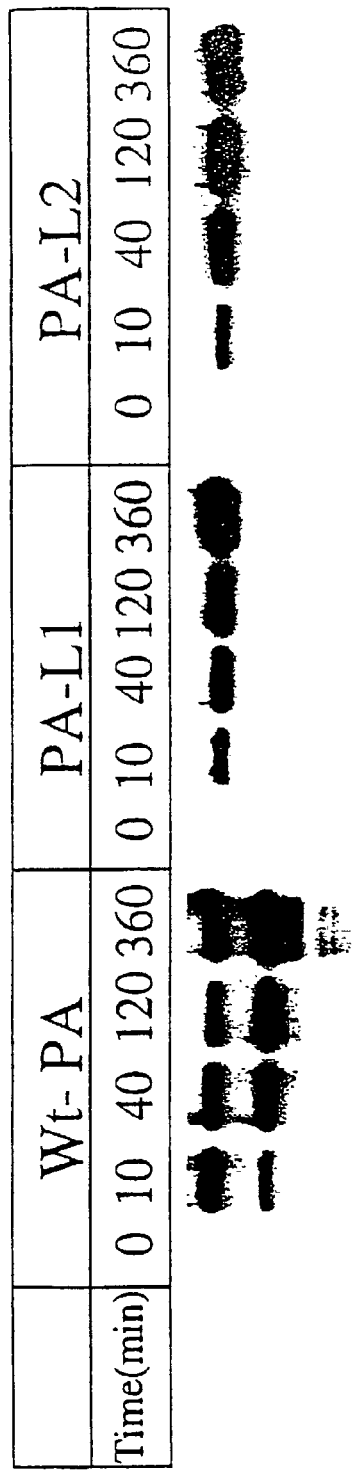
a
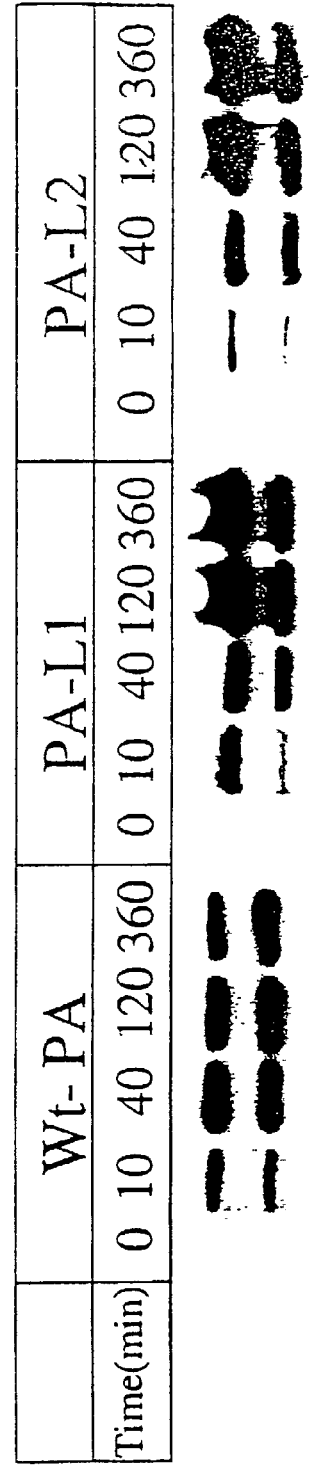
b

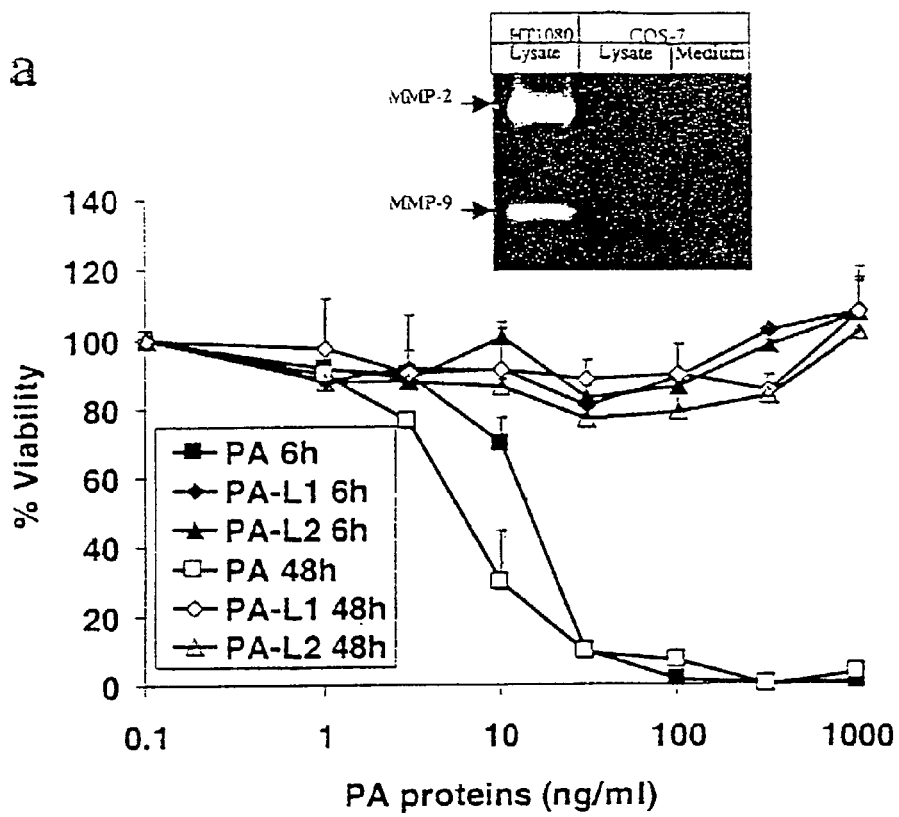
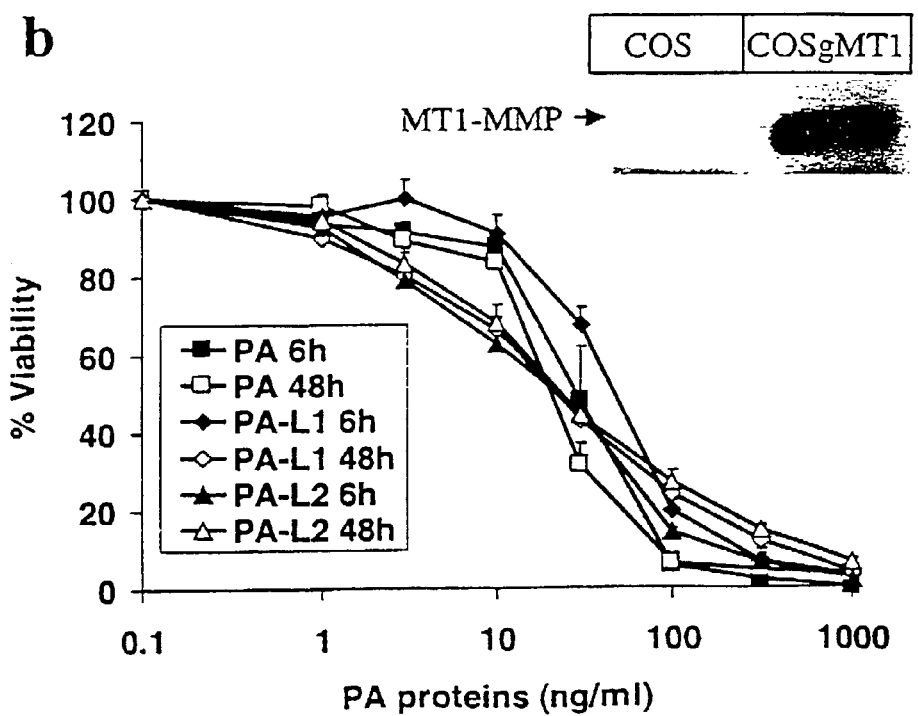
Fig. 8 a
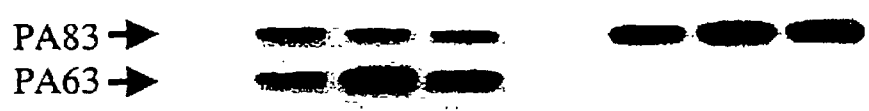
b
Fig. 13

SEQUENCE LISTING

```
<160> NUMBER OF SEQ ID NOS: 28

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:furin-like
      protease cleavage sequence

<400> SEQUENCE: 1

Arg Lys Lys Arg
  1

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:matrix
      metalloproteinase (MMP)-recognized cleavage site,
      gelatinase favorite substrate sequence

<400> SEQUENCE: 2

Gly Pro Leu Gly Met Leu Ser Gln
  1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:matrix
      metalloproteinase (MMP)-recognized cleavage site,
      gelatinase favorite substrate sequence

<400> SEQUENCE: 3

Gly Pro Leu Gly Leu Trp Ala Gln
  1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:tissue-type
      plasminogen activator (t-PA) and urokinase-type
      (u-PA) recognized cleavage site, physiological
      substrate sequence

<400> SEQUENCE: 4
```

```
Pro Cys Pro Gly Arg Val Val Gly Gly
 1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:
      urokinase-type plasminogen activator (u-PA)-recognized cleavage
      site, favorite sequence

<400> SEQUENCE: 5

Pro Gly Ser Gly Arg Ser Ala
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:
      urokinase-type plasminogen activator (u-PA)-recognized cleavage
      site, favorite sequence

<400> SEQUENCE: 6

Pro Gly Ser Gly Lys Ser Ala
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:tissue-type
      plasminogen activator (t-PA)-recognized cleavage
      site, favorite sequence

<400> SEQUENCE: 7

Pro Gln Arg Gly Arg Ser Ala
 1               5

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:5' primer F

<400> SEQUENCE: 8
aaaggagaac gtatatga                                                 18

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      phosphorylated primer R1
<220> FEATURE:
<221> NAME/KEY: modified_base
<222> LOCATION: (1)
<223> OTHER INFORMATION: n = phosphorylated t

<400> SEQUENCE: 9
ngagttcgaa gatttttgtt ttaattctgg                                    30
```

```
<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence:mutagenic
      phosphorylated sequence primer H1
<220> FEATURE:
<221> NAME/KEY: modified_base
<222> LOCATION: (1)
<223> OTHER INFORMATION: n = phosphorylated g

<400> SEQUENCE: 10
ngaccattag gaatgtggag tcaaagtaca agtgctggac ctacggttcc ag            52

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:reverse
      primer R2

<400> SEQUENCE: 11
acgtttatct cttattaaaa t                                              21

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence:
      phosphorylated mutagenic primer H2
<220> FEATURE:
<221> NAME/KEY: modified_base
<222> LOCATION: (1)
<223> OTHER INFORMATION: n = phosphorylated g

<400> SEQUENCE: 12
ngaccattag gattatgggc acaaagtaca agtgctggac ctacggttcc ag            52

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence:
      phosphorylated reverse primer R1
<220> FEATURE:
<221> NAME/KEY: modified_base
<222> LOCATION: (1)
<223> OTHER INFORMATION: n = phosphorylated t

<400> SEQUENCE: 13
nggtgagttc gaagattttt gttttaattc tgg                                 33

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence:mutagenic
      phosphorylated primer H1
<220> FEATURE:
<221> NAME/KEY: modified_base
<222> LOCATION: (1)
<223> OTHER INFORMATION: n = phosphorylated t

<400> SEQUENCE: 14
ngtccaggaa gagtagttgg aggaagtaca agtgctggac ctacggttcc ag            52
```

```
<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:encoded by
      mutagenic phosphorylated primer H1

<400> SEQUENCE: 15

Cys Pro Gly Arg Val Val Gly Gly
  1               5

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence:
      phosphorylated mutagenic primer H2
<220> FEATURE:
<221> NAME/KEY: modified_base
<222> LOCATION: (1)
<223> OTHER INFORMATION: n = phosphorylated g

<400> SEQUENCE: 16
ngaagtggaa gatcagcaag tacaagtgct ggacctacgg ttccag                 46

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:encoded by
      phosphorylated mutagenic primer H2

<400> SEQUENCE: 17

Gly Ser Gly Arg Ser Ala
  1               5

<210> SEQ ID NO 18
<211> LENGTH: 46
<212> TYPE: DNA
<213> ORGANISM: Artificial Sequence
<220> FEATURE:
<223> OTHER INFORMATION: Description of Artificial Sequence:
      phosphorylated mutagenic primer H3
<220> FEATURE:
<221> NAME/KEY: modified_base
<222> LOCATION: (1)
<223> OTHER INFORMATION: n = phosphorylated g

<400> SEQUENCE: 18
ngaagtggaa aatcagcaag tacaagtgct ggacctacgg ttccag                 46

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:encoded by
      phosphorylated mutagenic primer H3

<400> SEQUENCE: 19

Gly Ser Gly Lys Ser Ala
  1               5

<210> SEQ ID NO 20
```

-continued

<211> LENGTH: 46
<212> TYPE: DNA
<213> ORGANISM: Artificial Sequence
<220> FEATURE:
<223> OTHER INFORMATION: Description of Artificial Sequence:
phosphorylated mutagenic primer H4
<220> FEATURE:
<221> NAME/KEY: modified_base
<222> LOCATION: (1)
<223> OTHER INFORMATION: n = phosphorylated c

<400> SEQUENCE: 20
nagagaggaa gatcagcaag tacaagtgct ggacctacgg ttccag 46

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:encoded by
phosphorylated mutagenic primer H4

<400> SEQUENCE: 21

Gln Arg Gly Arg Ser Ala
1 5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:consensus
sequence minimized best substrate for u-PA

<400> SEQUENCE: 22

Ser Gly Arg Ser Ala
1 5

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence:PA sequence
at “furin loop”

<400> SEQUENCE: 23

Asn Ser Arg Lys Lys Arg Ser Thr Ser Ala Gly Pro Thr Val
1 5 10

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence:PA-U1
sequence at “furin loop”

<400> SEQUENCE: 24

Asn Ser Pro Cys Pro Gly Arg Val Val Gly Gly Ser Thr Ser Ala Gly
1 5 10 15

Pro Thr Val

<210> SEQ ID NO 25
<211> LENGTH: 17
<212> TYPE: PRT
<213> ORGANISM: Artificial Sequence
<220> FEATURE:

```
<223> OTHER INFORMATION: Description of Artificial Sequence:PA-U2
      sequence at "furin loop"

<400> SEQUENCE: 25

Asn Ser Pro Gly Ser Gly Arg Ser Ala Ser Thr Ser Ala Gly Pro Thr
 1               5                  10                  15
Val

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence:PA-U3
      sequence at "furin loop"

<400> SEQUENCE: 26

Asn Ser Pro Gly Ser Gly Lys Ser Ala Ser Thr Ser Ala Gly Pro Thr
 1               5                  10                  15
Val

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence:PA-U4
      sequence at "furin loop"

<400> SEQUENCE: 27

Asn Ser Pro Gln Arg Gly Arg Ser Ala Ser Thr Ser Ala Gly Pro Thr
 1               5                  10                  15
Val

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence:PA-U7
      sequence at "furin loop"

<400> SEQUENCE: 28

Asn Ser Pro Gly Gly Ser Thr Ser Ala Gly Pro Thr Val
 1               5                  10
```

MUTATED ANTHRAX TOXIN PROTECTIVE ANTIGEN PROTEINS THAT SPECIFICALLY TARGET CELLS CONTAINING HIGH AMOUNTS OF CELL-SURFACE METALLOPROTEINASES OR PLASMINOGEN ACTIVATOR RECEPTORS

CROSS-REFERENCES TO RELATED APPLICATIONS

This application claims priority to U.S. Ser. No. 60/155,961, filed Sep. 24, 1999, which is herein incorporated by reference in its entirety.

This application is related to U.S. Pat. No. 5,591,631; U.S. Pat. No. 5,677,274; and U.S. Ser. No. 08/937,276, filed Sep. 15, 1997; each herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Anthrax toxin is a three-part toxin secreted by *Bacillus anthracis* consisting of protective antigen (PA, 83 kDa), lethal factor (LF, 90 kDa) and edema factor (EF, 89 kDa) (Smith, H., et al., *J. Gen. Microbiol.*, 29:517-521 (1962); Leppla, S. H., *Sourcebook of bacterial protein toxins*, p. 277-302 (1991); Leppla, S. H., *Handb. Nat. Toxins*, 8:543-572 (1995)), which are individually non-toxic. The mechanism by which individual toxin components interact to cause toxicity was recently reviewed (Leppla, S. H., *Handb. Nat. Toxins*, 8:543-572 (1995)). Protective antigen, recognized as central, receptor-binding component, binds to an unidentified receptor (Escuyer, V., et al., *Infect. Immun.*, 59:3381-3386 (1991)) and is cleaved at the sequence $RKKR_{167}$ (SEQ ID NO: 1) by cell-surface furin or furin-like proteases (Klimpel, K. R., et al., *Proc. Natl. Acad. Sci. USA*, 89:10277-10281 (1992); Molloy, S. S., et al., *J. B. Chem.*, 267:16396-16402 (1992)) into two fragments: PA63, a 63 kDa C-terminal fragment, which remains receptor-bound; and PA20, a 20 kDa N-terminal fragment, which is released into the medium (Klimpel, K. R., et al., *Mol. Microbiol.*, 13:1094-1100 (1994)). Dissociation of PA20 allows PA63 to form heptamer (Milne, J. C., et al., *J. Biol. Chem.*, 269:20607-20612 (1994); Benson, E. L., et al., *Biochemistry*, 37:3941-3948 (1998)) and also bind LF or EF (Leppla, S. H., et al., *Bacterial protein toxins*, p. 111-112 (1988)). The resulting hetero-oligomeric complex is internalized by endocytosis (Gordon, V. M., et al., *Infect. Immun.*, 56:1066-1069 (1988)), and acidification of the vesicle causes insertion of the PA63 heptamer into the endosomal membrane to produce a channel through which LF or EF translocate to the cytosol (Friedlander, A. M., *J. Biol. Chem.*, 261:7123-7126 (1986)), where LF and EF induce cytotoxic events.

Thus, the combination of PA+LF, named anthrax lethal toxin, kills animals (Beal, F. A., et al., *J. Bacteriol.*, 83:1274-1280 (1962); Ezzell, J. W., et al., *Infect. Immun.*, 45:761-767 (1984)) and certain cultured cells (Friedlander, A. M., *J. Biol. Chem.*, 261:7123-7126 (1986); Hanna, P. C., et al., *Mol. Biol. Cell.*, 3:1267-1277 (1992)), due to intracellular delivery and action of LF, recently proven to be a zinc-dependent metalloprotease that is known to cleave at least two targets, mitogen-activated protein kinase kinase 1 and 2 (Duesbery, N. S., et al., *Science*, 280:734-737 (1998); Vitale, G., et al., *Biochem. Biophys. Res. Commun.*, 248:706-711 (1998)). The combination of PA+EF, named edema toxin, disables phagocytes and probably other cells, due to the intracellular adenylate cyclase activity of EF (Leppla, S. H., *Proc. Natl. Acad. Sci. USA.*, 79:3162-3166 (1982)).

LF and EF have substantial sequence homology in amino acid (aa) 1-250 (Leppla, S. H., *Handb. Nat. Toxins*, 8:543-572 (1995)), and a mutagenesis study showed this region constitutes the PA-binding domain (Quinn, C. P., et al., *J. Biol. Chem.*, 166:20124-20130 (1991)). Systematic deletion of LF fusion proteins containing the catalytic domain of *Pseudomonas* exotoxin A established that LF aa 1-254 (LFn) are sufficient to achieve translocation of "passenger" polypeptides to the cytosol of cells in a PA-dependent process (Arora, N., et al., *J. Biol. Chem.*, 267:15542-15548 (1992); Arora, N., et al., *J. Biol. Chem.*, 268:3334-3341 (1993)). A highly cytotoxic LFn fusion to the ADP-ribosylation domain of *Pseudomonas* exotoxin A, named FP59, has been developed (Arora, N., et al., *J. Biol. Chem.*, 268:3334-3341 (1993)). When combined with PA, FP59 kills any cell type which contains receptors for PA by the mechanism of inhibition of initial protein synthesis through ADP ribosylating inactivation of elongation factor 2 (EF-2), whereas native LF is highly specific for macrophages (Leppla, S. H., *Handb. Nat. Toxins*, 8:543-572 (1995)). For this reason, FP59 is an example of a potent therapeutic agent when specifically delivered to the target cells with a target-specific PA.

The crystal structure of PA at 2.1 Å was solved by X-ray diffraction (PDB accession 1ACC) (Petosa, C., et al., *Nature*, 385:833-838 (1997)). PA is a tall, flat molecule having four distinct domains that can be associated with functions previously defined by biochemical analysis. Domain 1 (aa 1-258) contains two tightly bound calcium ions, and a large flexible loop (aa 162-175) that includes the sequence $RKKR_{167}$ (SEQ ID NO:1), which is cleaved by furin during proteolytic activation. Domain 2 (aa 259-487) contains several very long β-strands and forms the core of the membrane-inserted channel. It is also has a large flexible loop (aa 303-319) implicated in membrane insertion. Domain 3 (aa 488-595) has no known function. Domain 4 (aa 596-735) is loosely associated with the other domains and is involved in receptor binding. For cleavage at $RKKR_{167}$ (SEQ ID NO: 1) is absolutely required for the subsequent steps in toxin action, it would be of great interest to engineer it to the cleavage sequences of some disease-associated proteases, such as matrix metalloproteinases (MMPs) and proteases of the plasminogen activation system (e.g., t-PA, u-PA, etc., see, e.g., Romer et al., *APMIS* 107:120-127 (1999)), which are typically overexpressed in tumors.

MMPs and plasminogen activators are families of enzymes that play a leading role in both the normal turnover and pathological destruction of the extracellular matrix, including tissue remodeling (Birkedal-Hansen, H., *Curr Opin Cell Biol*, 7:728-735 (1995); Alexander, C. M., et al., *Development*, 122:1723-1736 (1996)), angiogenesis (Schnaper, H. W, et al., *J Cell Physiol*, 156:235-246 (1993); Brooks, P. C., et al., *Cell*, 92:391-400 (1998)), tumor invasion and metastasis formation. The members of the MMP family are multidomain, zinc-containing, neutral endopeptidases and include the collagenases, stromelysins, gelatinases, and membrane-type metalloproteinases (Birkedal-Hansen, H., *Curr Opin Cell Biol*, 7:728-735 (1995)). It has been well documented in recent years that MMPs and proteins of the plasminogen activation system, e.g., plasmiogen activator receptors and plasminogen activators, are overexpressed in a variety of tumor tissues and tumor cell lines and are highly correlated to the tumor invasion and metastasis (Crawford, H. C., et al., *Invasion Metastasis*, 14:234-245 (1995); Garbisa, S., et al., Cancer Res., 47:1523-1528 (1987); Himelstein, B. P., et al., *Invest. Methods*, 14:246-258 (1995); Juarez, J., et al., *Int. J. Cancer*, 55:10-18 (1993); Kohn, E. C., et al., *Cancer Res.*, 55:1856-1862 (1995); Levy, A. T., et al, *Cancer Res.*, 51:439-444 (1991); Mignatti, P., et al., *Physiol. Rev.*, 73:161-195 (1993); Montgomery, A. M., et al., *Cancer Res.*, 53:693-700 (1993); Stetler-Stevenson, W. G., et al., *Annu. Rev Cell Biol*, 9:541-573 (1993); Stetler-Stevenson, W. G., *Invest. Methods*, 14:4664-4671 (1995); Davidson, B., et al., *Gynecol. Oncol.*, 73:372-382 (1999); Webber, M. M., et al., *Carcinogenesis*, 20:1185-1192 (1999); Johansson, N., et al., *Am J Pathol*, 154:469-480 (1999); Ries, C., et al., *Clin Cancer Res.*, 5:1115-1124 (1999); Zeng, Z. S., et al., *Carcinogenesis*, 20:749-755 (1999); Gokaslan, Z. L., et al., *Clin Exp Metastasis*, 16:721-728 (1998); Forsyth, P. A., et al., *Br J Cancer*, 79:1828-1835 (1999); Ozdemir, E., et al., *J Urol*, 161:1359-1363 (1999); Nomura, H., et al., *Cancer. Res.*, 55:3263-3266 (1995); Okada, Y., et al., *Proc. Natl. Acad. Sci. USA.*, 92:2730-2734 (1995); Sato, H., et al., *Nature*, 370:61-65 (1994); Chen, W. T., et al., *Ann N Y Acad Sci*, 878:361-371 (1999); Sato, T., et al., *Br J Cancer*, 80:1137-43 (1999); Polette, M., et al., *Int J Biochem cell Biol.*, 30:1195-1202 (1998); Kitagawa, Y., et al., *J Urol.*, 160:1540-1545; Nakada, M., et al., *Am J Pathol.*, 154:417-428 (1999); Sato, H., et al., *Thromb Haemost*, 78:497-500 (1997)).

Among the MMPs, MMP-2 (gelatinase A), MMP-9 (gelatinase B) and membrane-type 1 MMP (MT1-MMP) are reported to be most related to invasion and metastasis in various human cancers (Crawford, H. C., et al., *Invasion Metastasis*, 14:234-245 (1995); Garbisa, S., et al., *Cancer Res.*, 47:1523-1528 (1987); Himelstein, B. P., et al., *Invest. Methods*, 14:246-258 (1995); Juarez, J., et al., *Int. J. Cancer*, 55:10-18 (1993); Kohn, E. C., et al., *Cancer Res.*, 55:1856-1862 (1995); Levy, A. T., et al., *Cancer Res.*, 51:439-444 (1991); Mignatti, P., et al., *Physiol. Rev.*, 73:161-195 (1993); Montgomery, A. M., et al., *Cancer Res.*, 53:693-700 (1993); Stetler-Stevenson, W. G., et al., *Annu Rev Cell Biol*, 9:541-573 (1993); Stetler-Stevenson, W. G., *Invest. Methods*, 14:4664-4671 (1995); Davidson, B., et al., *Gynecol. Oncol.*, 73:372-382 (1999); Webber, M. M., et al., *Carcinogenesis*, 20:1185-1192 (1999); Johansson, N., et al., *Am J Pathol*, 154:469-480 (1999); Ries, C., et al., *Clin Cancer Res.*, 5:1115-1124 (1999); Zeng, Z. S., et al., *Carcinogenesis*, 20:749-755 (1999); Gokaslan, Z. L., et al., *Clin Exp Metastasis*, 16:721-728 (1998); Forsyth, P. A., et al., *Br J Cancer*, 79:1828-1835 (1999); Ozdemir, E., et al., *J Urol*, 161:1359-1363 (1999); Nomura, H., et al., *Cancer. Res.*, 55:3263-3266 (1995); Okada, Y., et al., *Proc. Natl. Acad. Sci. USA.*, 92:2730-2734 (1995); Sato, H., et al., *Nature*, 370:61-65 (1994); Chen, W. T., et al., *Ann N Y Acad Sci*, 878:361-371 (1999); Sato, T., et al., *Br J Cancer*, 80:1137-43 (1999); Polette, M., et al., *Int J Biochem cell Biol.*, 30:1195-1202 (1998); Kitagawa, Y., et al., *J Urol.*, 160:1540-1545; Nakada, M., et al., *Am J Pathol.*, 154:417-428 (1999); Sato, H., et al., *Thromb Haemost*, 78:497-500 (1997)). The important role of MMPs during tumor invasion and metastasis is to break down tissue extracellular matrix and dissolution of epithelial and endothelial basement membranes, enabling tumor cells to invade through stroma and blood vessel walls at primary and secondary sites. MMPs also participate in tumor neoangiogenesis and are selectively upregulated in proliferating endothelial cells in tumor tissues (Schnaper, H. W, et al., *J Cell Physiol*, 156:235-246 (1993); Brooks, P. C., et al., *Cell*, 92:391-400 (1998); Chambers, A. F., et al., *J Natl Cancer Inst*, 89:1260-1270 (1997)). Furthermore, these proteases can contribute to the sustained growth of established tumor foci by the ectodomain cleavage of membrane-bound pro-forms of growth factors, releasing peptides that are mitogens for tumor cells and/or tumor vascular endothelial cells (Arribas, J., et al., *J Biol Chem*, 271:11376-11382 (1996); Suzuki, M., et al., *J Biol Chem*, 272:31730-31737 (1997)).

However, catalytic manifestations of MMP and plasminogen activators are highly regulated. For example, the MMPs are expressed as inactive zymogen forms and require activation before they can exert their proteolytic activities. The activation of MMP zymogens involves sequential proteolysis of N-terminal propeptide blocking the active site cleft, mediated by proteolytic mechanisms, often leading to an autoproteolytic event (Springman, E. B., et al., *Proc Natl Acad Sci USA*, 87:364-368 (1990); Murphy, G., et al., *APMIS*, 107:38-44 (1999)). Second, a family of proteins, the tissue inhibitors of metalloproteinases (TIMPs), are correspondingly widespread in tissue distribution and function as highly effective MMP inhibitors (Ki~$10^{-10}$ M) (Birkedal-Hansen, H., et al., *Crit. Rev Oral Biol Med*, 4:197-250 (1993)). Though the activities of MMPs are tightly controlled, invading tumor cells that utilize the MMP's degradative capacity somehow circumvent these negative regulatory controls, but the mechanisms are not well understood.

The contributions of MMPs in tumor development and metastatic process lead to the development of novel therapies using synthetic inhibitors of MMPs (Brown, P. D., *Adv Enzyme Regul*, 35:293-301 (1995); Wojtowicz-Praga, S., et al., *J Clin Oncol*, 16:2150-2156 (1998); Drummond, A. H., et al., *Ann N Y Acad Sci*, 30:228-235 (1999)). Among a multitude of synthetic inhibitors generated, Marimastat is already clinically employed in cancer treatment (Drummond, A. H., et al., *Ann N Y Acad Sci*, 30:228-235 (1999)).

Here, as an alternate to the use of MMP inhibitors, we explored a novel strategy using modified PAs which could only be activated by MMPs or plasminogen activators to specially kill MMP- or and plasminogen activators-expressing tumor cells. PA mutants are constructed in which the furin recognition site is replaced by sequences susceptible to cleavage by MMPs or and plasminogen activators. When combined with LF or an LF fusion protein comprising the PA binding site, these PA mutants are specifically cleaved by cancer cells, exposing the LF binding site and translocating the LF or LF fusion protein into the cell, thereby specifically delivering a compounds, e.g., a therapeutic or diagnostic agent, to the cell.

SUMMARY OF THE INVENTION

Matrix metalloproteinases ("MMPs") and proteins of the plasminogen activation system (e.g., t-PAR, u-PAR, u-PA, t-PA) are overexpressed in a variety of tumor tissues and tumor cell lines and are highly correlated to tumor invasion and metastasis. In addition, these proteins are overexpressed in other cells such as inflammatory cells. Here we constructed anthrax toxin protective antigen (PA) mutants, in which the furin site is replaced by sequences specifically cleaved by MMPs or plasminogen activators. These MMP or plasminogen activator targeted PA mutants are only activated by plasminogen activator- or MMP-expressing tumor cells, so as to specifically deliver a toxin, a diagnostic, or a therapeutic agent. The activation occurs primarily on the cell surface, resulting in translocation and delivery of the compounds. The compounds can be diagnostic or therapeutic agents. Preferably the compounds are delivered to the cells of a human subject suffering from cancer, thereby killing the cancer cells and treating the cancer.

In one aspect, the present invention provides a method of targeting a compound to a cell over-expressing a matrix metalloproteinase, a plasminogen activator, or a plasminogen activator receptor, the method comprising the steps of: (i) administering to the cell a mutant PA protein comprising a matrix metalloproteinase or a plasminogen activator-recognized cleavage site in place of the native PA furin-recognized cleavage site, wherein the mutant PA is cleaved by a matrix metalloproteinase or a plasminogen activator; and (ii) administering to the cell a compound comprising an LF polypeptide comprising a PA binding site; wherein the LF polypeptide binds to cleaved PA and is translocated into the cell, thereby delivering the compound to the cell.

In one embodiment, the cell overexpresses a matrix metalloproteinase. In another embodiment, the matrix metalloproteinase is selected from the group consisting of MMP-2 (gelatinase A), MMP-9 (gelatinase B) and membrane-type 1 MMP (MT1-MMP). In another embodiment, the matrix metalloproteinase-recognized cleavage site is selected from the group consisting of GPLGMLSQ (SEQ ID NO:2) and GPLGLWAQ (SEQ ID NO:3).

In one embodiment, the cell overexpresses a plasminogen activator or a plasminogen activator receiptor. In another embodiment, the plasminogen activator is selected from the group consisting of t-PA (tissue-type plasminogen activator) and u-PA (urokinase-type plasminogen activator). In another embodiment, the plasminogen activator-recognized cleavage site is selected from the group consisting of PCPGRVVGG, PGSGRSA, PGSGKSA, and PQRGRSA (SEQ ID NOS:4-7, respectively).

In one embodiment, the cell is a cancer cell. In another embodiment, the cancer is selected from the group consisting of lung cancer, breast cancer, bladder cancer, thyroid cancer, liver cancer, lung cancer, pleural cancer, pancreatic cancer, ovarian cancer, cervical cancer, colon cancer, fibrosarcoma, neuroblastoma, glioma, melanoma, monocytic leukemia, and myelogenous leukemia. In another embodiment, the cell is an inflammatory cell. In another embodiment, the cell is a human cell.

In one embodiment, the lethal factor polypeptide is native lethal factor. In another embodiment, the compound is native lethal factor.

In one embodiment, the lethal factor polypeptide is linked to a heterologous compound. In another embodiment, the compound is a diagnostic or a therapeutic agent. In another embodiment, the compound is shiga toxin, A chain of diphtheria toxin, or *Pseudomonas* exotoxin A. In another embodiment, the compound is a detectable moiety or a nucleic acid.

In one embodiment, the compound is covalently linked to lethal factor via a chemical bond. In another embodiment, the heterologous compound is recombinantly linked to lethal factor.

In one embodiment, the mutant PA protein is a fusion protein comprising a heterologous receptor binding domain. In another embodiment, the heterologous receptor binding domain is selected from the group consisting of a single chain antibody and a growth factor.

In one aspect, the present invention provides an isolated mutant protective antigen protein comprising a matrix metalloproteinase or a plasminogen activator-recognized cleavage site in place of the native protective antigen furin-recognized cleavage site, wherein the mutant protective antigen is cleaved by a matrix metalloproteinase or a plasminogen activator.

In one embodiment, the matrix metalloproteinase or a plasminogen activator-recognized cleavage site is selected from the group consisting of PCPGRVVGG, PGSGRSA, PGSGKSA, PQRGRSA, GPLGMLSQ and GPLGLWAQ (SEQ ID NOS:4-7, 2 and 3, respectively).

BRIEF DESCRIPTION OF THE DRAWINGS

FIG. 1. Generation of PA mutants can be specifically processed by MMPs. (A). Schematic representation of MMP substrate PA mutants. The furin cleavage site RKKR (SEQ ID NO:1) was replaced with gelatinase favorite substrate sequences GPLGMLSQ (SEQ ID NO:2) in PA-L1 and GPLGLWAQ (SEQ ID NO:3) in PA-L2. The arrows show the cleavage sites of furin or MMPs as indicated. (B). Cleavage of PA-L1 by MMP-2, MMP-9 and soluble form furin. As described in Materials and Methods, PA-L1 was incubated with MMP-2, MMP-9 and furin, respectively, aliquots were withdrawn at the time points indicated, and the samples were analyzed by western blotting with the rabbit polyclonal antibody against PA. (C). Cleavage of PA-L2 by MMP-2, MMP-9 and soluble form furin. PA-L2 was treated as in B. (D). Cleavage of WT-PA by MMP-2, MMP-9 and soluble form furin. WT-PA was treated as in B.

FIG. 3. Cytotoxicity of PA-L1 and PA-L2 (A) or nicked form of them (B) to the MMP non-expressing Vero cells. As described in Materials and Methods, Vero cells were cultured in 96-well plates to 80-100% confluence washed and replaced with serum-free DMEM medium. Then different concentrations (from 0 to 1000 ng/ml) of WT-PA, PA-L1 and PA-L2, or MMP-2 nicked PA-L1 and PA-L2 combined with FP59 (constant at 50 ng/ml) were separately added to the cells. The toxins were left in the medium for 48 hours, or removed and replaced with fresh serum-containing DMEM after 6 hour. MTT was added to determined cell viability at 48 hours. Nicked PA-L1 and PA-L2 were prepared by cleavage of PA-L1 and PA-L2 by active MMP-2 at 37° C. for 3 hours as described in Materials and Methods.

FIG. 4. Cytotoxicity of PA-L1 and PA-L2 to the MMP expressing tumor HT1080 cells (A), A2058 cells (B) and MDA-MB-231 cells. As described in Materials and Methods, HT1080 and A2058 cells were cultured to 80-100% confluence, washed and replaced with serum-free DMEM medium. Then different concentrations (from 0 to 1000 ng/ml) of WT-PA, PA-L1 and PA-L2 combined with FP59 (constant at 50 ng/ml) were separately added to the cells and incubated for 6 hours and 48 hours. MTT was added to determined cell viability at 48 hours.

FIG. 5. Effect of MMP inhibitors on cytotoxicity of PA-L1 and PA-L2 to HT1080 cells. HT1080 cells were cultured to 80% confluence in a 96-well plate, and washed twice with serum-free DMEM. Then MMP inhibitors GM6001, BB94 and BB2516 were added to the cells at final concentration of 10 µM in serum-free DMEM. After 300 min pre-incubation with the MMP inhibitors, WT-PA, PA-L1 and PA-L2 (300 ng/ml) combined with FP59 (50 ng/ml) were separately added to the cells and incubated for 6 hours. After that, the medium containing the toxins and MMP inhibitors were removed, and fresh serum-containing medium was added and incubation continued to 48 hours. MTT was added to determine cell viability as described in Materials and Methods.

FIG. 6. PA-L1 and PA-L2 selectively killed MMP-expressing tumor cells in a co-culture model. As described in Materials and Methods, Vero, HT1080, MDA-MB-231 and A2058 cells were cultured in the separate chambers of 8-chamber slides to 80 to 100% confluence. Then the slides with partitions removed were put into 100 mm petri dishes with serum-free medium, so that the different cells were in the same culture environment. WT-PA, PA-L1 or PA-L2 (300 ng/ml) each combined with FP59 (50 ng/ml) were separately added to the cells, and incubated to 48 hours. MTT was added to determine cell viability. Insert, after 48 hours toxin challenge MTT was added to the cells, live cells converted MTT to blue dye, which precipitated in cytosol, while dead cells remained colorless.

FIG. 8. The role of transfected MT1-MMP in cytotoxicity of PA-L1 and PA-L2 to COS-7 cells. A. Cytotoxicity of PA-L1 and PA-L2 to COS-7 cells. As described in Materials and Methods, COS-7 cells were cultured to 80-100% of confluence, washed and replaced with serum-free DMEM medium. Then different concentrations (from 0 to 1000 ng/ml) of WT-PA, PA-L1 and PA-L2 combined with FP59 (constant at 50 ng/ml) were separately added to the cells and incubated for 6 hours and 48 hours. MTT was added to determined cell viability at 48 hours. Insert: Zymographic analysis of cell extracts and culture supernatants of COS-7 as described in Materials and Methods, using supernatant of HT1080 as control. B. Cytotoxicity of PA-L1 and PA-L2 to CosgMT1. CosgMT1 cells were treated the same as in A. Insert: Comparison expression of MT1-MMP from COS-7 and CosgMT1 cells by western blotting using a rabbit anti-MT1-MMP antibody (AB815, CHEMICON International, Inc.).

FIG. 9. Generation of mutated PA proteins which can be specifically cleaved by uPA or tPA. Cleavage of PA and mutated PA proteins by soluble form of furin (in panel a), uPA (in panel b) or tPA (in panel c). Proteins were incubated with furin, uPA or tPA, for the times indicated and samples were analyzed by SDS-PAGE and Commassie staining in panel a, or diluted and analyzed by Western blotting with rabbit polyclonal antibody against PA in panel b and c.

FIG. 10. Binding and processing of pro-uPA by different cell lines. Vero cells, Hela cells, A2058 cells, and Bowes cells were cultured in 24-well plate to confluence, washed and incubated in serum-free media with 1 μg/ml of pro-uPA and 1 μg/ml of glu-plasminogen for 1 h, then the cell lysates were prepared for Western blotting analysis with monoclonal antibody against uPA B-chain (#394).

FIG. 11. Cytotoxicity of mutated PA proteins for UPAR expressing tumor cells. Hela cells (in panel a), A2058 cells (in panel b), and Bowes cells (in panel c) were cultured to 50% confluence, washed and replaced with seruum-free DMEM containing 100 ng/ml of pro-uPA and 1 μg/ml of glu-plasminogen. Then different concentrations (from 0 to 1000 ng/ml) of PA, PA-U1, PA-U2, PA-U3, PA-U4, and PA-U7 together with FP59 (constant at 50 ng/ml) were incubated with the cells for 6 h. Then the toxins were removed and replaced with fresh serum-containing DMEM. MTT was added to determined cell viability at 48 h.

FIG. 12. Cytotoxicity of mutated PA proteins for uPAR non-expressing Vero cells. a. Vero cells were cultured in 96-well plates to 50% confluence, washed and replaced with serum-free DMEM containing 100 ng/ml of pro-uPA and 1 μg/ml of glu-plasminogen. Then the cells were treated with toxins as above. B. Vero cells were treated as in panel a, except that nicked PA-U2 was used for the cytotoxicity assay. Nicked PA-U2 was prepared by cleavage of PA-U2 with uPA at 37° C. for 1 h as described in Materials and Methods.

FIG. 13. Binding and proteolytic activation of PA and PA-U2 on the surface of Vero cells (in panel a) and Hela (in panel b) cells. Vero and Hela cells were cultured in 24-well plates to confluence, washed and changed serum-free medium containing 100 ng/ml of pro-uPA and 1 μg/ml of plasminogen with or without PAI-1 (2 μg/ml). Then PA and PA-U2 were added to the cells with a final concentration of 1000 ng/ml, incubated for 30 min or 120 min. The cell lysates were prepared for Western blotting analysis using rabbit anti-PA polyclonal antibody (#5308) to check the processing status of PA and PA-U2 and the effect of PAI-1 on it.

FIG. 14. Effects of PAI-1 on cytotoxicity of PA-U2 to tumor cells. Hela cells (in panel a), A2058 cells (in panel b), and Bowes cells (in panel c) were cultured to 50% confluence in a 96-well plate, washed and incubated with serum-free DMEM containing 100 ng/ml of pro-uPA and 1 μg/ml of glu-plasminogen with or without 2 μg/ml of PAI-1, for 30 min. Then different concentrations of PA and PA-U2 (from 0 to 1000 ng/ml) combined with FP59 (50 ng/ml) were separately added to the cells and incubated for 6 hours. After that, the toxins were removed and replaced with fresh serum-containing DMEM. MTT was added to determined cell viability at 48 h.

FIG. 15. Effects of blocking uPAR on cytotoxicity of PA-U2 to the tumor cells. a. Effects of ATE on cytotoxicity of PA-U2 to Hela, A2058, and Bowes cells. b. Effects of uPAR blocking antibody R3 on cytotoxicity of PA-U2 to Hela, A2058, and Bowes cells. Cells were cultured to 50% confluence, washed and incubated with serum-free DMEM containing 100 ng/ml of pro-uPA and 1 g/ml of glu-plasminogen, and different concentrations of ATF or uPAR blocking antibody R3. Then PA and PA-U2 (300 ng/ml each) combined with FP59 (50 ng/ml) were added to the cells and incubated for 6 hours. After that, the toxins were removed and replaced with fresh serum-containing DMEM. MTT was added to determined cell viability at 48 h.

FIG. 16. PA-U2 selectively killed uPAR-expressing Hela cells in a co-culture model. Vero and Hela cells were cultured in the separate chambers of 8-chamber slides to confluence. Then the slides with partitions removed were put into 100 mm petri dishes with serum-free medium containing 100 ng/ml of pro-uPA and 1 μg/ml of glu-plasminogen, so that the different cells were in the same culture environment. PA and PA-U2 (1000 ng/ml) each combined with FP59 (50 ng/ml) were separately added to the cells, and incubated to 48 hours. MTT was added to determine cell viability. Insert, PA-U2 was selectively proteolytically activated on Hela cells in a co-culture model. The cells were treated the same as in A, except that after 2 h incubation with toxins the cells were washed and lysed, and the processing status of PA proteins were detected by anti-PA antibody as in FIG. 14.

FIG. 17. Cytotoxicity of PA-U2, PA-U3, and PA-U4 on tPA expressing cells. Bowes cells (a) and HUVEC cells (b) were cultured to 50% confluence, washed and replaced with serum-free DMEM without pro-uPA and glu-plasminogen. Then the cells were treated with different concentrations (from 0 to 1000 ng/ml) of PA, PA-U2, PA-U3, and PA-U4 together with FP59 (constant at 50 ng/ml) for 12 h. MTT was added to determine cell viability at 48 h.

DETAILED DESCRIPTION

I. Introduction

Figure 2:
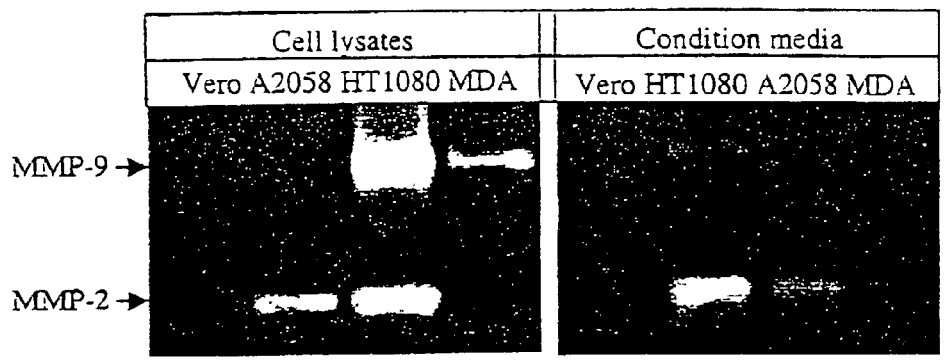
FIG. 2. Zymographic analysis of the gelatinases associated with serum-free conditioned media (A) or Triton X-100 extracts (B) of Vero cells, HT1080 cells and A2058 cells. 1 mg of cell extract protein, or volumes of conditioned medium (3-4 ml) normalized to the protein concentration of the corresponding cell extracts were analyzed by gelatin zymography as described in Materials and Methods.

Proteolytic degradation of the extracellular matrix plays a crucial role both in cancer invasion and non-neoplastic tissue remoldeling, and in both cases it is accomplished by a number of proteases. Best known are the plasminogen activation system that leads to the formation of the serine protease plasmin, and a number of matrix metalloproteinase, including collagenases, gelatinases and stromelysins (Dano, K., et al., *APMIS*, 107:120-127 (1999)). The close association between MMP and plasminogen activator overexpression and tumor metastasis has been noticed for a decade. For example, the contributions of MMPs in tumor development and metastatic process lead to the development of novel therapies using synthetic inhibitors of MMPs (Brown, P. D., *Adv Enzyme Regul*, 35:293-301 (1995); Wojtowicz-Praga, S., et al., *J Clin Oncol*, 16:2150-2156 (1998); Drummond, A. H., et al., *Ann N Y Acad Sci*, 30:228-235 (1999)). However, these inhibitors only slow growth and do not eradicate the tumors. The present study is the first effort to use bacterial toxins modified to target MMPs and plasminogen activators, which are highly expressed and employed by tumor cells for invasion. Mutant PA molecules in which the furin cleavage site is replaced by an MMP or plasminogen activator target site can be used to deliver compounds such as toxins to the cell, thereby killing the cell. The compounds have the ability to bind PA through their interaction with LF and are translocated by PA into the cell. The PA and LF-comprising compounds are administered to cells or subjects, preferably mammals, more preferably humans, using techniques known to those of skill in the art. Optionally, the PA and LF-comprising compounds are administered with a pharmaceutically acceptable carrier.

The compounds typically are either native LF or an LF fusion protein, i.e., those that have a PA binding site (approximately the first 250 amino acids of LF, Arora et al., *J. Biol. Chem.* 268:3334-3341 (1993)) fused to another polypeptide or compound so that the protein or fusion protein binds to PA and is translocated into the cell, causing cell death (e.g., recombinant toxin FP59, anthrax toxin lethal factor residue 1-254 fusion to the ADP-ribosylation domain of *Pseudomonas* exotoxin A). The fusion is typically chemical or recombinant. The compounds fused to LF include, e.g., therapeutic or diagnostic agent, e.g., native LF, a toxin, a bacterial toxin, shiga toxin, A chain of diphtheria toxin, *Pseudomonas* exotoxin A, a protease, a growth factor, an enzyme, a detectable moiety, a chemical compound, a nucleic acid, or a fusion polypeptide, etc.

The mutant PA molecules of the invention can be further targeted to a specific cell by making mutant PA fusion proteins. In these mutant fusion proteins, the PA receptor binding domain is replaced by a protein such as a growth factor or other cell receptor ligand specifically expressed on the cells of interest. In addition, the PA receptor binding domain may be replaced by an antibody that binds to an antigen specifically expressed on the cells of interest.

These proteins provide a way to specifically kill tumor cells without serious damage to normal cells. This method can also be applied to non-cancer inflammatory cells that contain high amounts of cell-surface associated MtPs or plasminogen activators. These PA mutants are thus useful as therapeutic agents to specifically kill tumor cells.

We constructed two PA mutants, PA-L1 and PA-L2, in which the furin recognition site is replaced by sequences susceptible to cleavage by MMPs, especially by MMP-2 and MMP-9. When combined with FP59, these two PA mutant proteins specifically killed MMP-expressing tumor cells, such as human fibrosarcoma HT1080 and human melanoma A2058, but did not kill MMP non-expressing cells. Cytotoxicity assay in the co-culture model, in which all the cells were in the same culture environment and were equal accessible to the toxins in the supernatant, showed PA-L1 and PA-L2 specifically killed only MMP-expressing tumor cells HT1080 and A2058, not Vero cells. This result demonstrated activation processing of PA-L1 and PA-L2 mainly occurred on the cell surfaces and mostly contributed by the membrane-associated MMPs, so the cytotoxicity is restricted to MMP-expressing tumor cells. TIMPs are widely present in extracellular milieu and inhibit MMP activity in supernatants. PA proteins bind to the cells very quickly with maximum binding happened within 60 min. In contrast to secreted MMPs, membrane-associated MMPs express their proteolytic activities more efficiently by anchoring on cell membrane and enjoying two distinct advantageous properties, which are highly focused on extracellular matrix substrates and more resistant to proteinase inhibitors present in extracellular milieu.

Recently it has been shown physiological concentrations of plasmin can activate both MMP-2 and MMP-9 on cell surface of HT1080 by a mechanism independent of MMP or acid proteinase activities (Mazzieri, R., et al., *EMBO J*, 16:2319-2332 (1997)). In contrast, in soluble phase plasmin degrades both MMP-2 and MMP-9 (Mazzieri, R., et al., *EMBO J*, 16:2319-2332 (1997)). Thus, plasmin may provide a mechanism keeping gelatinase activities on cell surface to promote cell invasion. It has been well established MT1-MMP functions as both activator and receptor of MMP-2, but has no effect on MMP-9 (see review Polette, M., et al., *Int J Biochem cell Biol.*, 30:1195-1202 (1998); Sato, H., et al., *Thromb Haemost*, 78:497-500 (1997)). A MMP-2/TIMP-2 complex binds to MT1-MMP on cell surface, which serves as a high-affinity site, then be proteolytically activated by an adjacent MT1-MMP, which serves as an activator. Recent works have shown that adhesion receptors, such as $\alpha v\beta 3$ integrin (Brooks, P. C., et al., *Cell*, 85:683-693 (1996)) and cell surface hyaluronan receptor CD44 (Tu, Q., et al, *Gene Development*, 13:35-48 (1999)), may provide means to retain soluble active MMP-2 or MMP-9 to invasive tumor cell surface, where their proteolytic activities are most likely to promote cell invasion. For MMP activities involved in tumor invasion and metastasis are localized and/or modulated on the cell surface in insoluble phase, this makes MMPs an ideal target for tumor tissues.

It was originally thought that the role of MMPs and plasminogen activators was simply to break down tissue barriers to promote tumor invasion and metastasis. It is now understood, for example, that MMPs also participate in tumor neoangiogenesis and are selectively upregulated in proliferating endothelial cells. Therefore, these modified bacterial toxins may have the advantageous properties that targeted to not only tumor cells themselves but may also the dividing vascular endothelial cells which essential to neoangiogenesis in tumor tissues. Therefore, the MMP targeted toxins may also kill tumor cells by starving the cells of necessary nutrients and oxygen.

The mutant PA molecules of the invention can also be specifically targeted to cells using mutant PA fusion proteins. In these fusion proteins, the receptor binding domain of PA is replaced with a heterologous ligand or molecule such as an antibody that recognizes a specific cell surface protein. PA protein has four structurally distinct domains for performing the functions of receptor binding and translocation of the catalytic moieties across endosomal membranes (Petosa, C., et al., *Nature,* 385:833-838 (1997)). Domain 4 is the receptor-binding domain and has limited contacts with other domains (Petosa, C., et al., *Nature,* 385:833-838 (1997)). Therefore, PA can be specifically targeted to alternate receptors or antigens specifically expressed by tumors by replacing domain 4 with the targeting molecules, such as single-chain antibodies or a cytokines used by other immuntoxins (Thrush, G. R., et al., *Annu Rev Immunol,* 14:49-71 (1996)). For example, PA-L1 and PA-L2 are directed to alternate receptors, such as GM-CSF receptor, which is highly expressed in leukemias cells and solid tumors including renal, lung, breast and gastrointestinal carcinomas (Thrush, G. R., et al., *Annu Rev Immunol,* 14:49-71 (1996); 74-79). It should be highly expected that the combination of these two independent targeting mechanism should allow tumors to be more effectively targeted, and side effects such as hepatotoxicity and vascular leak syndrome should be significantly reduced.

With respect to the plasminogen activation system, two plasminogen activators are known, the urokinase-type plasminogen activator (uPA) and the tissue-type plasminogen activator (tPA), of which uPA is the one primarily involved in extracellular matrix degradation (Dano, K., et al., *APMIS,* 107:120-127 (1999)). uPA is a 52 kDa serine protease which is secreted as an inactive single chain proenzyme (pro-uPA) (Nielsen, L. S., et al., *Biochemistry,* 21:6410-6415 (1982); Petersen, L. C., et al., *J. Biol. Chem.,* 263:11189-11195 (1988)). The binding domain of pro-uPA is the epidermal growth factor-like amino-terminal fragment (ATE; aa 1-135, 15 kDa) that binds with high affinity (Kd=0.5 mM) to urokinase-type plasminogen activator receptor (uPAR) (Cubellis, M. V., et al., *Proc. Natl. Acad. Sci. U.S.A.,* 86:4828-4832 (1989)), a GPI-linked receptor. uPAR is a 60 kDa three domain glycoprotein whose N-terminal domain 1 contains the high affinity binding site for ATF of pro-uPA (Ploug, M., et al., *J. Biol. Chem.,* 266:1926-1933 (1991); Behrendt, N., et al., *J. Biol. Chem.,* 266:7842-7847 (1991)). uPAR is overexpressed on a variety of tumors, including monocytic and myelogenous leukemias (Lanza, F., et al., *Br. J. Haematol.,* 103:110-123 (1998); Plesner, T., et al., *Am. J. Clin. Pathol.,* 102:835-841 (1994)), and cancers of the breast (Carriero, M. V., et al., *Clin. Cancer Res.,* 3:1299-1308 (1997)), bladder (Hudson, M. A., et al., *J. Natl. Cancer Inst.,* 89:709-717 (1997)), thyroid (Ragno, P., et al., *Cancer Res.,* 58:1315-1319 (1998)), liver (De Petro, G., et al., *Cancer Res.,* 58:2234-2239 (1998)), pleura (Shetty, S., et al., *Arch. Biochem. Biophys.,* 356:265-279 (1998)), lung (Morita, S., et al., *Int. J. Cancer,* 78:286-292 (1998)), pancreas (Taniguchi, T., et al., *Cancer Res.,* 58:4461-4467 (1998)), and ovaries (Sier, C. F., et al., *Cancer Res.,* 58:1843-1849 (1998)). Pro-uPA binds to uPAR by ATF, while the binding process does not block the catalytic, carboxyl-terminal domain. By association with UPAR, pro-uPA gets near to and subsequently activated by trace amounts of plasmin bound to the plasma membrane by cleavage of the single chain pro-uPA within an intra-molecular loop held closed by a disulfide bridge. Thus the active uPA consists of two chains (A+B) held together by this disulfide bond (Ellis, V., et al., *J. Biol. Chem.,* 264:2185-2188 (1989)).

Plasminogen is present at high concentration (1.5-2.0 µM) in plasma and interstitial fluids (Dano, K., et al., *Adv. Cancer Res.,* 44:139-266 (1985)). Low affinity, high capacity binding of plasminogen to cell-surface proteins through the lysine binding sites of plasminogen kringles enhances considerably the rate of plasminogen activation by uPA (Ellis, V., et al., *J. Biol. Chem.,* 264: 2185-2188 (1989); Stephens, R. W., et al., *J. Cell Biol.,* 108:1987-1995 (1989)). Active uPA has high specificity for Arg560-Val561 bond in plasminogen, and cleavage between these residues gives rise to more plasmin that is referred to as "reciprocal zymogen activation" (Petersen, L. C., *Eur. J. Biochem.,* 245:316-323 (1997)). The result of this system is efficient generation of active uPA and plasmin on cell surface. In this context, uPAR serves as a template for binding and localization of pro-uPA near to its substrate plasminogen on plasma membrane.

Unlike uPA, plasmin is a relatively non-specific protease, cleaving many glycoproteins and proteoglycans of the extracellular matrix, as well as fibrin (Liotta, L. A., et al., *Cancer Res.,* 41:4629-4636 (1981)). Therefore, cell surface bound plasmin mediates the non-specific matrix proteolysis which facilitates invasion and metastasis of tumor cells through restraining tissue structures. In addition, plasmin can activate some of the matrix metalloproteases which also degrade tissue matrix (Werb, Z., et al., *N. Engl. J. Med.,* 296:1017-1023 (1977); DeClerck, Y. A., et al., *Enzyme Protein,* 49:72-84 (1996)). Plasmin can also activate growth factors, such as TGF-β, which may further modulate stromal interactions in the expression of enzymes and tumor neo-angiogenesis (Lyons, R. M., et al., *J. Cell Biol.,* 106:1659-1665 (1988)). Plasminogen activation by uPA is regulated by two physiological inhibitors, plasminogen activator inhibitor-1 and 2 (PAI-1 and PAI-2) (Cubellis, M. V., et al., *Proc. Natl. Acad. Sci. U.S.A.,* 86:4828-4832 (1989); Ellis, V., et al., *J. Biol. Chem.,* 265:9904-9908 (1990); Baker, M. S., et al., *Cancer Res.,* 50:4676-4684 (1990)), by formation 1:1 complex with uPA. Plasmin generated in the cell surface plasminogen activation system is relatively protected from its principle physiological inhibitor α2-antiplasmin (Ellis, V., et al., *J. Biol. Chem.,* 266: 12752-12758 (1991)).

Cancer invasion is essentially a tissue remodeling process in which normal tissue is substituted with cancer tissue. Accumulated data from preclinical and clinical studies strongly suggested that the plasminogen activation system plays a central role in the processes leading to tumor invasion and metastasis (Andreasen, P. A., et al., *Int. J. Cancer,* 72:1-22 (1997); Chapman, H. A., *Curr. Opin. Cell Biol.,* 9:714-724 (1997); Schmitt, M., et al., *Thromb. Haemost.,* 78:285-296 (1997)). High levels of uPA, uPAR and PAL-1, but decreased PAI-2 are associated with poor disease outcome (Schmitt, M., et al., *Thromb. Haemost.,* 78:285-296 (1997)). In situ hybridization studies of the tumor tissues have shown usually cancer cells highly expressed uPAR, while tumor stromal cells expressed pro-uPA, which subsequently binds to uPAR on the surface of cancer cells where it is activated and thereby generating plasmin (Pyke, C., et al., *Am. J. Pathol.,* 138:1059-1067 (1991)). For the activation of pro-uPA is highly restricted to the tumor cell surface, it may be an ideal target for cancer treatment.

uPA and tPA possess an extremely high degree of structure similarity (Lamba, D., et al., *J. Mol. Biol.,* 258:117-135 (1996); Spraggon, G., et al., *Structure,* 3:681-691 (1995)), share the same primary physiological substrate (plasminogen) and inhibitors (PAI-1 and PAI-2) (Cohen, D., et al., *Blood,* 78:3114-3124 (1991)), and exhibit restricted substrate specificity. By using substrate phage display and substrate subtraction phage display approaches, recent investigations had identified substrates that discriminate between uPA and tPA, showing the consensus substrate sequences with high selectivity by uPA or tPA (Ke, S. H., et at, *J. Biol. Chem.,* 272:20456-20462 (1997); Ke, S. H., et al, *J. Biol. Chem.,* 272:16603-16609 (1997)). To exploit the unique characteristics of the uPA plasminogen system and anthrax toxin in the design of tumor cell selective cytotoxins, in the work described here, mutated anthrax PA proteins were constructed in which the furin site is replaced by sequences susceptible to specific cleavage by uPA. These uPAR/uPA-targeted PA proteins were activated selectively on the surface of uPAR-expressing tumor cells in the present of pro-uPA, and caused internalization of a recombinant cytotoxin FP59 to selectively kill the tumor cells. Also, a mutated PA protein was generated which selectively killed tissue-type plasminogen activator expressing cells.

II. Methods of Producing PA and LF Constructs

A. Construction Nucleic Acids Encoding PA Mutants, LF, and PA and LF Fusion Proteins PA includes a cellular receptor binding domain, a translocation domain, and an LF binding domain. The PA polypeptides of the invention have at least a translocation domain and an LF binding domain. In the present invention, mature PA (83 kDa) is one preferred embodiment. In addition to full length recombinant PA, amino-terminal deletions up to the 63 kDa cleavage site or additions to the full length PA are useful. A recombinant form of processed PA is also biologically active and could be used in the present invention. PA fusion proteins in which the receptor binding domain have been deleted can also be constructed, to target PA to specific cell types. Although the foregoing and the prior art describe specific deletion and structure-function analysis of PA, any biologically active form of PA can be used in the present invention.

Amino-terminal residues 1-254 of LF are sufficient for PA binding activity. Amino acid residues 199-253 may not all be required for PA binding activity. One embodiment of LF is amino acids 1-254 of native LF. Any embodiment that contains at least about amino acids 1-254 of native LF can be used in the present invention, for example, native LF. Nontoxic embodiments of LF are preferred.

PA and LF fusion proteins can be produced using recombinant nucleic acids that encode a single-chain fusion proteins. The fusion protein can be expressed as a single chain using in vivo or in vitro biological systems. Using current methods of chemical synthesis, compounds can be also be chemically bound to PA or LF. The fusion protein can be tested empirically for receptor binding, PA or LF binding, and internalization following the methods set forth in the Examples.

In addition, functional groups capable of forming covalent bonds with the amino- and carboxyl-terminal amino acids or side groups of amino acids are well known to those of skill in the art. For example, functional groups capable of binding the terminal amino group include anhydrides, carbodiimides, acid chlorides, and activated esters. Similarly, function-al groups capable of forming covalent linkages with the terminal carboxyl include amines and alcohols. Such functional groups can be used to bind compound to LF at either the amino- or carboxyl-terminus. Compound can also be bound to LF through interactions of amino acid residue side groups, such as the SH group of cysteine (see, e.g., Thorpe et al., *Monoclonal Antibody-Toxin Conjugates: Aiming the Magic Bullet*, in *Monoclonal Antibodies in Clinical Medicine*, pp. 168-190 (1982); Waldmann, *Science*, 252: 1657 (1991); U.S. Pat. Nos. 4,545,985 and 4,894,443). The procedure for attaching an agent to an antibody or other polypeptide targeting molecule will vary according to the chemical structure of the agent. As example, a cysteine residue can added at the end of LF. Since there are no other cysteines in LF, this single cysteine provides a convenient attachment point through which to chemically conjugate other proteins through disulfide bonds. Although certain of the methods of the invention have been described as using LF fusion proteins, it will be understood that other LF compositions having chemically attached compounds can be used in the methods of the invention.

Protective antigen proteins can be produced from nucleic acid constructs encoding mutants, in which the naturally occurring furin cleavage site has been replaced by an MMP or a plasminogen activator cleavage site. In addition, LF proteins, and LF and PA fusion proteins can also be expressed from nucleic acid constructs according to standard methodology. Those of skill in the art will recognize a wide variety of ways to introduce mutations into a nucleic acid encoding protective antigen or to construct a mutant protective antigen-encoding nucleic acid. Such methods are well known in the art (see Sambrook et al., *Molecular Cloning, A Laboratory Manual* ($2^{nd}$ ed. 1989); Kriegler, *Gene Transfer and Expression: A Laboratory Manual* (1990); and *Current Protocols in Molecular Biology* (Ausubel et al., eds., 1994)). In some embodiments, nucleic acids of the invention are generated using PCR (see, e.g., Examples I and III). For example, using overlap PCR protective antigen encoding nucleic acids can be generated by substituting the nucleic acid subsequence that encodes the furin site with a nucleic acid subsequence that encodes a matrix metalloproteinase (MMP) site (e.g., GPLG-MLSQ and GPLGLWAQ; SEQ ID NOS:2 ands 3) (see, e.g., Example I). Similarly, an overlap PCR method can be used to construct the protective antigen proteins in which the furin site is replaced by a plasminogen activator cleavage site (e.g., the uPA and tPA physiological substrate sequence PCPGRV-VGG (SEQ ID NO:4), the uPA favorite sequence PGSGRSA (SEQ ID NO:5), the uPA favorite sequence PGSGKSA (SEQ ID NO:6), or the tPA favorite sequence PQRGRSA (SEQ ID NO:7)) (see, e.g., Example III).

B. Expression of LF, PA and LF and PA Fusion Proteins

To obtain high level expression of a nucleic acid (e.g., cDNA, genomic DNA, PCR product, etc. or combinations thereof) encoding a native (e.g., PA) or mutant protective antigen protein (e.g., PA-L1, PA-L2, PA-U1, PA-U2, PA-U3, PA-U4, etc.), LF, or a PA or LF fusion protein, one typically subclones the protective antigen encoding nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the protective antigen encoding nucleic acid are available in, e.g., *E. coli*, *Bacillus* sp., and *Salmonella* (Palva et al., *Gene* 22:229-235 (1983)). Kits for such expression systems are commercially available. Eukaryotic expression systems for mammalian cells, yeast, and insect cells are well known in the art and are also commercially available.

In some embodiment, protective antigen containing proteins are expressed in non-virulent strains of *Bacillus* using *Bacillus* expression plasmids containing nucleic acid sequences encoding the particular protective antigen protein (see, e.g., Singh, Y., et al., *J Biol Chem.*, 264:19103-19107 (1989)). The protective antigen containing proteins can be isolated from the *Bacillus* culture using protein purification methods (see, e.g., Varughese, M., et al., *Infect Immun*, 67:1860-1865 (1999)).

The promoter used to direct expression of a protective antigen encoding nucleic acid depends on the particular application. The promoter is preferably positioned about the same distance from the heterologous transcription start site as it is from the transcription start site in its natural setting. As is known in the art, however, some variation in this distance can be accommodated without loss of promoter function. The promoter typically can also include elements that are responsive to transactivation, e.g., Gal4 responsive elements, lac repressor responsive elements, and the like. The promoter can be constitutive or inducible, heterologous or homologous.

In addition to the promoter, the expression vector typically contains a transcription unit or expression cassette that contains all the additional elements required for the expression of the nucleic acid in host cells. A typical expression cassette thus contains a promoter operably linked, e.g., to the nucleic acid sequence encoding the protective antigen containing protein, and signals required for efficient expression and termination and processing of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from bacterial proteins, or mammalian proteins such as tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination and processing, if desired. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a protective antigen encoding nucleic acid under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the protective antigen containing protein, which is recovered from the culture using standard techniques identified below.

III. Purification of Polypeptides of the Invention

Recombinant proteins of the invention can be purified from any suitable expression system, e.g., by expressing the proteins in *B. anthracis* and then purifying the recombinant protein via conventional purification techniques (e.g., ammonium sulfate precipitation, ion exchange chromatography, gel filtration, etc.) and/or affinity purification, e.g., by using antibodies that recognize a specific epitope on the protein or on part of the fusion protein, or by using glutathione affinity gel, which binds to GST (see, e.g., Scopes, *Protein Purification: Principles and Practice* (1982); U.S. Pat. No. 4,673,641; Ausubel et al., supra; and Sambrook et al., supra). In some embodiments, the recombinant protein is a fusion protein with GST or Gal4 at the N-terminus. Those of skill in the art will recognize a wide variety of peptides and proteins that can be fused to the protective antigen containing protein to facilitate purification (e.g., maltose binding protein, a polyhistidine peptide, etc.).

A. Purification of Proteins from Recombinant Bacteria

Recombinant and native proteins can be expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2-3 passages through a French press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The protein of choice is separated from other bacterial proteins by standard separation techniques, e.g., ion exchange chromatography, ammonium sulfate fractionation, etc.

B. Standard Protein Separation Techniques for Purifying Proteins of the Invention Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. Alternatively, the protein of interest in the supernatant can be further purified using standard protein purification techniques. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein, e.g., PA-U1, etc., can be used to isolated the protein from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein of choice can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

In some embodiments, the proteins are purified from culture supernatants of *Bacillus* (see, e.g., Examples I and III). Briefly, the proteins are purified by making a culture supernatant 5 mM in EDTA, 35% saturated in ammonium sulfate and 1% in phenyl-Sepharose Fast Flow (Pharmacia). The phenyl-Sepharose Fast Flow is then agitated and collected. The collected resin is washed with 35% saturated ammonium sulfate and the protective antigens were then eluted with 10 mM HEPES-1 mM EDTA (pH 7.5). The proteins can then be further purified using a MonoQ column (Pharmacia Biotech). The proteins can be eluted using a NaCl gradient in 10 mM CHES (2-[N-cyclohexylamino]ethanesulfonic acid)-0.06% (vol/vol) ethanolamine (pH 9.1). The pooled MonoQ fractions can then be dialyzed against the buffer of choice for subsequent analysis or applications.

IV. Assays for Measuring Changes in Cell Growth

The administration of a functional PA and LF combination of the invention to a cell can inhibit cellular proliferation of certain cell types that overexpress MMPs and proteins of the plasminogen activation system, e.g., cancer cells, cells involved in inflammation, and the like. One of skill in the art can readily identify functional proteins and cells using methods that are well known in the art. Changes in cell growth can be assessed by using a variety of in vitro and in vivo assays, e.g., MTT assay, ability to grow on soft agar, changes in contact inhibition and density limitation of growth, changes in growth factor or serum dependence, changes in the level of tumor specific markers, changes in invasiveness into Matrigel, changes in cell cycle pattern, changes in tumor growth in vivo, such as in transgenic mice, etc.

The term "over-expressing" refers to a cell that expresses a matrix metalloproteinase, a plasminogen activator or a plasminogen activator receptor mRNA or protein in amounts at least about twice that normally produced in a reference normal cell type, e.g., a Vero cell. Overexpression can result, e.g., from selective pressure in culture media, transformation, activation of endogenous genes, or by addition of exogenous genes. Overexpression can be analyzed using a variety of assays known to those of skill in the art to determine if the gene or protein is being overexpressed (e.g., northerns, RT-PCR, westerns, immunoassays, cytotoxicity assays, growth inhibition assays, enzyme assays, gelatin zymography, etc.). An example of a cell overexpressing a matrix metalloproteinase are the tumor cell lines, fibrosarcoma HT1080, melanoma A2058 and breast cancer MDA-MB-231. An example of a cell which does not overexpress a matrix metalloproteinase is the non-tumor cell line Vero. An example of a cells that overexpress a plasminogen activator receptor are the uPAR overexpressing cell types Hela, A2058, and Bowes. An example of a cell which does not overexpress a plasminogen activator receptor is the non-tumor cell line Vero. An example of a cells that overexpress a tissue-type plasminogen activator are cell types human melanoma Bowes and human primary vascular endothelial cells. An example of a cell which does not overexpress a plasminogen activator receptor is the non-tumor cell line Vero.

A. Assays for Changes in Cell Growth by Administration of Protective Antigen and Lethal Factor One or more of the following assays can be used to identify proteins of the invention which are capable of regulating cell proliferation. The phrase "protective antigen constructs" refers to a protective antigen protein of the invention. Functional protective antigen constructs identified by the following assays can then be used to treat disease and conditions, e.g., to inhibit abnormal cellular proliferation and transformation. Thus, these assays can be sued to identify protective antigen proteins that are useful in conjunction with lethal factor containing proteins to inhibit cell growth of tumors, cancers, cancerous cells, and other pathogenic cell types.

Soft Agar Growth or Colony Formation in Suspension

Soft agar growth or colony formation in suspension assays can be used to identify protective antigen constructs, which when used in conjunction with a LF construct, inhibit abnormal cellular proliferation and transformation. Typically, transformed host cells (e.g., cells that grow on soft agar) are used in this assay. Techniques for soft agar growth or colony formation in suspension assays are described in Freshney, *Culture of Animal Cells a Manual of Basic Technique,* $3^{rd}$ ed., Wiley-Liss, New York (1994), herein incorporated by reference. See also, the methods section of Garkavtsev et al. (1996), supra, herein incorporated by reference.

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Administration of an active protective antigen protein and an active LF containing protein to transformed cells would reduce or eliminate the host cells' ability to grow in stirred suspension culture or suspended in semi-solid media, such as semi-solid or soft. This is because the transformed cells would regenerate anchorage dependence of normal cells, and therefore require a solid substrate to grow. Therefore, this assay can be used to identify protective antigen constructs that can function with a lethal factor protein to inhibit cell growth. Once identified, such protective antigen constructs can be used in a number of diagnostic or therapeutic methods, e.g., in cancer therapy to inhibit abnormal cellular proliferation and transformation.

Contact Inhibition and Density Limitation of Growth

Contact inhibition and density limitation of growth assays can be used to identify protective antigen constructs which are capable of inhibiting abnormal proliferation and transformation in host cells. Typically, transformed host cells (e.g., cells that are not contact inhibited) are used in this assay. Administration of a protective antigen construct and a lethal factor construct to these transformed host cells would result in cells which are contact inhibited and grow to a lower saturation density than the transformed cells. Therefore, this assay can be used to identify protective antigen constructs which are useful in compositions for inhibiting cell growth. Once identified, such protective antigen constructs can be used in disease therapy to inhibit abnormal cellular proliferation and transformation.

Alternatively, labeling index with [$^3$H]-thymidine at saturation density can be used to measure density limitation of growth. See Freshney (1994), supra. The transformed cells, when treated with a functional PA/LF combination, regenerate a normal phenotype and become contact inhibited and would grow to a lower density. In this assay, labeling index with [$^3$H]-thymidine at saturation density is a preferred method of measuring density limitation of growth. Transformed host cells are treated with a protective antigen construct and a lethal factor construct (e.g., LP59) and are grown for 24 hours at saturation density in non-limiting medium conditions. The percentage of cells labeling with [$^3$H]-thymidine is determined autoradiographically. See, Freshney (1994), supra. The host cells treated with a functional protective antigen construct would give arise to a lower labeling index compared to control (e.g., transformed host cells treated with a non-functional protective antigen construct or non-functional lethal factor construct).

Growth Factor or Serum Dependence

Growth factor or serum dependence can be used as an assay to identify functional protective antigen constructs. Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. When a tumor suppressor gene is transfected and expressed in these transformed cells, the cells would reacquire serum dependence and would release growth factors at a lower level. Therefore, this assay can be used to identify protective antigen constructs which are able to act in conjunction with a lethal factor to inhibit cell growth. Growth factor or serum dependence of transformed host cells which are transfected with a protective antigen construct can be compared with that of control (e.g., transformed host cells which are treated with a non-functional protective antigen or non-functional lethal factor). Transformed host cells treated with a functional protective antigen would exhibit an increase in growth factor and serum dependence compared to control.

Tumor Specific Markers Levels

Tumor cells release an increased amount of certain factors (hereinafter "tumor specific markers") than their normal counterparts. For example, tumor angiogenesis factor (TAF) is released at a higher level in tumor cells than their normal counterparts. See, e.g., Folkman, Angiogenesis and cancer, *Sem Cancer Biol*. (1992)).

Tumor specific markers can be assayed for to identify protective antigen constructs, which when administered with a lethal factor construct, decrease the level of release of these markers from host cells. Typically, transformed or tumorigenic host cells are used. Administration of a protective antigen and a lethal factor to these host cells would reduce or eliminate the release of tumor specific markers from these cells. Therefore, this assay can be used to identify protective antigen constructs are functional in suppressing tumors.

Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); whur et al., *Br. J. Cancer* 42:305-312 (1980); Gulino, *Angiogenesis, tumor vascularization, and potential interference with tumor growth*. In Mihich, E. (ed): "Biological Responses in Cancer." New York, Plenum (1985); Freshney *Anticancer Res.* 5:111-130 (1985).

Cytotoxicity Assay with MTT

The cytotoxicity of a particular PA/LF combination can also be assayed using the MTT cytotoxicity assay. Cells are seeded and grown to 80 to 100% confluence. The cells are then were washed twice with serum-free DMEM to remove residual FCS and contacted with a particular PA/LF combination. MTT (3-[4,5-dimethylthiazol-2-yl]-2,5-diphenyltetrazolium bromide) is then added to the cells and oxidized MTT (indicative of a live cell) is solubilized and quantified.

Invasiveness into Matrigel

The degree of invasiveness into Matrigel or some other extracellular matrix constituent can be used as an assay to identify protective antigen constructs which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used. Administration of an active protective antigen/ lethal factor protein combination to these tumorigenic host cells would decrease their invasiveness. Therefore, functional protective antigen constructs can be identified by measuring changes in the level of invasiveness between the tumorigenic cells before and after the administration of the protective antigen and lethal factor constructs.

Techniques described in Freshney (1994), supra, can be used. Briefly, the level of invasion of tumorigenic cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}I$ and counting the radioactivity on the distal side of the filter or bottom of the dish. See, e.g., Freshney (1984), supra.

$G_0/G_1$ Cell Cycle Arrest Analysis $G_0/G_1$ cell cycle arrest can be used as an assay to identify functional protective antigen construct. PA/LF construct administration can cause G1 cell cycle arrest. In this assay, cell lines can be used to screen for functional protective antigen constructs. Cells are treated with a putative protective antigen construct and a lethal factor construct. The cells can be transfected with a nucleic acid comprising a marker gene, such as a gene that encodes green fluorescent protein. Administration of a functional protective antigen/lethal factor combination would cause $G_0/G_1$ cell cycle arrest. Methods known in the art can be used to measure the degree of $G_1$ cell cycle arrest. For example, the propidium iodide signal can be used as a measure for DNA content to determine cell cycle profiles on a flow cytometer. The percent of the cells in each cell cycle can be calculated. Cells exposed to a functional protective antigen would exhibit a higher number of cells that are arrested in $G_0/G_1$ phase compared to control (e.g., treated in the absence of a protective antigen).

Tumor Growth In Vivo

Effects of PA/LFon cell growth can be tested in transgenic or immune-suppressed mice. Transgenic mice can be made, in which a tumor suppressor is disrupted (knock-out mice) or a tumor promoting gene is overexpressed. Such mice can be used to study effects of protective antigen as a method of inhibiting tumors in vivo.

Knock-out transgenic mice can be made by insertion of a marker gene or other heterologous gene into a tumor suppressor gene site in the mouse genome via homologous recombination. Such mice can also be made by substituting the endogenous tumor suppressor with a mutated version of the tumor suppressor gene, or by mutating the endogenous tumor suppressor, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecehi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

These knock-out mice can be used as hosts to test the effects of various protective antigen constructs on cell growth. These transgenic mice with a tumor suppressor gene knocked out would develop abnormal cell proliferation and tumor growth. They can be used as hosts to test the effects of various protective antigen constructs on cell growth. For example, introduction of protective antigen constructs and lethal factor constructs into these knock-out mice would inhibit abnormal cellular proliferation and suppress tumor growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. In hosts which developed invasive tumors, cells are exposed to a protective antigen construct/lethal factor combination (e.g., by subcutaneous injection). After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, functional protective antigen constructs which are capable of inhibiting abnormal cell proliferation can be identified. This model can also be used to identify functional mutant versions of protective antigen.

V. Pharmaceutical Compositions Administration

Protective antigen containing proteins and lethal factor containing proteins can be administered directly to the patient, e.g., for inhibition of cancer, tumor, or precancer cells in vivo, etc. Administration is by any of the routes normally used for introducing a compound into ultimate contact with the tissue to be treated. The compounds are administered in any suitable manner, preferably with pharmaceutically acceptable carriers. Suitable methods of administering such compounds are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985)). For example, if in vivo delivery of a biologically active protective antigen protein is desired, the methods described in Schwarze et al. (see *Science* 285:1569-1572 (1999)) can be used.

The compounds, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient ("a therapeutically effective amount"), in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound or vector in a particular patient In determining the effective amount of the compound(s) to be administered in the treatment or prophylaxis of cancer, the physician evaluates circulating plasma levels of the respective compound(s), progression of the disease, and the production of anti-compound antibodies. In general, the dose equivalent of a compound is from about 1 ng/kg to 10 mg/kg for a typical patient. Administration of compounds is well known to those of skill in the art (see, e.g., Bansinath et al., *Neurochem Res.* 18:1063-1066 (1993); Iwasaki et al., *Jpn. J. Cancer Res.* 88:861-866 (1997); Tabrizi-Rad et al., *Br. J. Pharmacol.* 111:394-396 (1994)).

For administration, compounds of the present invention can be administered at a rate determined by the LD-50 of the particular compound, and its side-effects at various concentrations, as applied to the mass and overall health of the patient. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Construction of Mutant PA with Matrix Metalloproteinase Cleavage Sites

A. Materials

Enzymes for DNA manipulation and modification were purchased from New England Biolabs (Beverly, Mass.). FP59 and soluble form furin were prepared in our laboratory according to standard methodology. Active MMP-2 was a kind gift from Dr. William Stetler-Stevenson, active form MMP-9 was purchased from CALBIOCHEM (San Diego, Calif.). MMP inhibitors BB-94 (Batimastat) and BB-2516 (Marimastat) were kind gifts from British Biotechnology Limited, GM6001 was a kind gift from Dr. Richard E. Galardy prepared as described (Grobelny, D., et al., *Biochemistry,* 31:7152-7154 (1992)). Rabbit anti-PA polyclonal antibody (#5308) was made in our laboratory. Rabbit anti-MT-MMP1 (AB815) was purchased from CHEMICON International, Inc. (Temecula, Calif.). The sequence for LF can be found, e.g., in Robertson & Leppla, Gene 44: 71-78 (1986). The sequence for PA is described, e.g., in Singh et al., *J. Biol. Chem.* 264: 19103-19107 (1989) (expression vector pYS5); Leppla, in *Methods in Enzymology*, vol. 165, pp. 103-116 (Harshman ed., 1988). Site-directed mutagenesis of PA molecules has been previously described (Singh et al., *J. Biol. Chem.* 269: 29039-29046 (1994)

Construction of PA MMP Substrate Mutants

Overlap PCR was used to construct the PA mutants with the furin site replaced by MMP substrate octapeptide GPLGMLSQ (SEQ ID NO:2) in PA-L1 and GPLGLWAQ (SEQ ID NO:3) in PA-L2. Wild type PA (WT-PA) expression plasmid pYS5 (Singh, Y., et al., *J Biol Chem,* 264:19103-19107 (1989)) was used as template. We used 5' primer F (AAAGGAGAACGTATATGA (SEQ ID NO:8), underlined are SD sequence and start codon of PA) and the phosphorylated primer R1 (pTGAGTTCGAAGATTTTTGTTTTAATTCTGG (SEQ ID NO:9), annealing to the sequence corresponding to $P_{154}$-$S_{163}$) to amplify the fragment N. We used the mutagenic phosphorylated primer H1 (pGGACCATTAGGAATGTGGAGTCAAAGTACAAGTGC TGGACCTACGGTTCCG (SEQ ID NO:10), encoding MMP substrate GPLGMLSQ (SEQ ID NO:2) and $S_{168}$-$P_{176}$) and reverse primer R2 ACGTTTATCTCTTATTAAAAT (SEQ ID NO:11), annealing to the sequence compassing $I_{589}$-$R_{595}$) to amplify the mutagenic fragment M1. We used a phosphorylated mutagenic primer H2 (pGGACCAT TAGGATTATGGGCACAAAGTACAAGTGCTGGACCTACGGTTCCG (SEQ ID NO:12), encoding MMP substrate GPLGLWAQ (SEQ ID NO:3) and $S_{168}$-$P_{176}$) to amplify mutagenic fragment M2. Then used primer F and R2 to amplify the ligation products of N and M1, N and M2, respectively, resulting in the mutagenic fragments L1 and L2, in which the coding sequence for furin site ($RKKR_{167}$; SEQ ID NO:1) were replaced by MMP substrate sequence GPLGMLSQ and GPLGLWAQ (SEQ ID NOS:2 and 3), respectively. The HindIII/PstI digests of L1 and L2, which included the mutation sites, were cloned between HindIII and PstI site of pYS5. The resulting expression plasmids were named pYS-PA-L1 and pYS-PA-L2, their expression products, the PA mutated proteins, were accordingly named PA-L1 and PA-L2.

Expression and Purification of WT-PA, PA-L1 and PA-L2

To express WT-PA, PA-L1 and PA-L2, expression plasmids pYS5, pYS-PA-L1 and pYS-PA-L2 were transformed into non-virulent strain *B. anthracis* UM23C1-1, and grown in FA medium (Singh, Y., et al, *J Biol Chem,* 264:19103-19107 (1989)) with 20 μg/ml of kanamycin for 16 h at 37° C., PA proteins were purified by ammonium sulfate precipitation followed by monoQ column (Pharmacia Biotech) chromatography, as described previously (Varughese, M., et al., *Infect Immun,* 67:1860-1865 (1999)).

In Vitro Cleavage of WT-PA, PA-L1 and PA-L2 by Furin, MMP-2 and MMP-9

To test whether PA-L1 and PA-L2 had the ability to be processed by MMP-2 and MMP-9 rather than furin, in vitro cleavage of WT-PA, PA-L1 and PA-L2 were performed. For furin cleavage, 50 μl volume of reaction in PBS, pH 7.4, 25 mM HEPES, 0.2 mM EDTA, 0.2 mM EGTA, 100 μg/ml ovalbumin, 1.0 mM $CaCl_2$, 1.0 mM $MgCl_2$, including 5 μg of WT-PA, PA-L1 and PA-L2, respectively. Digestion was started by addition 0.1 µg of soluble form of furin and incubated at 37° C., aliquots (5 µl) were withdrawn at different time points. Cleavage was detected by western blotting with a rabbit anti-PA antibody. For western blotting, the sample aliquots were separated by PAGE using 10-20% gradient Tris-glycine gel (Novex, San Diego, Calif.) and electroblotted to a nitrocellulose membrane (Novex, San Diego, Calif.). The membrane was blocked with 5% (w/v) non-fat milk and hybridized by using rabbit anti-PA polyclonal antibody (#5308). Blot was washed and incubated with an HRP-conjugated goat anti-rabbit antibody (sc-2004, Santa Cruz Biotechnology, Inc., Santa Cruz, Calif.) and was visualized by TMB Stabilized Substrate for HRP (Promega, Madison, Wis.). For MMP-2 and MMP-9 cleavage, 5 µg each of WT-PA, PA-L1 and PA-L2 was incubated with 0.2 µg active MMP-2 or 0.2 µg active MMP-9, respectively, in 50 µl of reactions including 50 mM HEPES, pH 7.5, 10 mM $CaCl_2$, 200 mM NaCl, 0.05% (v/v) Brij-35 and 50 µM $ZnSO_4$. Aliquots (5 µl) were withdrawn at different time points and were analyzed by western blotting with rabbit anti-PA polyclonal antibody (#5308) as described above.

Cells and Culture Medium

Vero cells, COS-7 cells, human fibrosarcoma HT1080 cells, human melanoma A2058 cells and human breast cancer MDA-MB-231 cells were obtained from ATCC (Rockville, Md.). All cells were grown in Dulbecco' Modified Eagle's Medium (DMEM) with 0.45% glucose, 10% fetal bovine serum, 2 mM glutamine. Cells were maintained at 37° C. in a 5% $CO_2$ incubator. Cells were dissociated with a solution of 0.05% trypsin, 0.02% EDTA, 0.01 M sodium phosphate, pH 7.4, and were usually subcultured at a split ratio of 1:4.

Preparation of Cell Extracts and Condition Media for Gelatin Zymography

Cells were cultured in 75 $cm^2$ flask to 80-100% of confluence at 37° C. in DMEM supplemented with 10% FCS. Then the cells were washed twice with serum-free DMEM to remove residual FCS, and lysed for 10 min on ice with 1 ml/flask of 0.5% (v/v) Triton X-100 in 0.1 M Tris-HCl, pH 8.0, and scraped with a rubber policeman. The cell lysates were centrifuged at 10,000 rpm for 10 min at 4° C., the concentrations of the proteins were determined by BCA Protein Assay Kit (PIERCE, Rockford, Ill.), and was adjusted to 1 mg/ml by lysis buffer. For collection the conditioned media, the cells were incubated for 24 h with 4 ml/flask of serum-free DMEM. The culture supernatants were harvested, and cellular debris removed by centrifugation at 10,000 rpm for 10 min at 4° C. Cell lysates and conditioned media were frozen at −70° C. or immediately processed for zymographic analysis.

Gelatin Zymography

Cell extracts (1 ml) or conditioned media normalized to protein concentrations of the corresponding cell extract (3-4 ml) were incubated at 4° C. for 1 h in an end-over-end mixer with 50 µl of gelatin-sepharose 4B (Pharmacia Biotech AB) equilibrated with 50 mM Tris-HCl, 150 mM NaCl, 5 mM $CaCl_2$, 0.02% (v/v) Tween-20, 10 mM EDTA, pH 7.5. After 4 washes with 1 ml of equilibration buffer containing 200 mM NaCl, the beads were resuspended in 30 µl 4× non-reducing sample buffer, centrifuged to collect the supernatants and loaded on 10% gelatin zymogram gel (Novex, San Diego, Calif.). After electrophoresis, the gel was soaked in Renaturing Buffer (Novex, San Diego, Calif.) for twice with 30 min each to renature gelatinases at room temperature. The gel was then equilibrated in Developing Buffer (Novex, San Diego, Calif.), which added back a divalent metal cation required for enzymatic activity, first for 30 min at room temperature and then in new buffer at 37° C. for overnight. The gel was then stained overnight with 0.5% (w/v) Commassie Brilliant Blue R-250 in 45% (v/v) methanol, 10% acetic acid and destained in the same solution without dye.

Cytotoxicity Assay with MTT

Cytotoxicity of WT-PA, PA-L1 and PA-L2 to the test cells were performed in 96-well plates. Cells were properly seeded into 96-well plates so that they reached 80 to 100% of confluence the next day. The cells were washed twice with serum-free DMEM to remove residual FCS. Then serially diluted WT-PA, PA-L1 or PA-L2 (from 0 to 1000 ng/ml) combined with FP59 (50 ng/ml) in serum-free DMEM were added to the cells to give a total volume of 200 µl/well. One group of cells was challenged with the toxins for 6 hours, then removed the toxins replaced with fresh DMEM supplemented with 10% FCS. For the cytotoxic action of FP59 relies on inhibition of initial protein synthesis by ADP ribosylating EF-2 and usually need 24-48 hours to show the toxicity, cytotoxicity was allowed to develop for 48 hours. After that cell viability was assayed by adding 50 µl of 2.5 mg/ml MTT (3-[4,5-dimethylthiazol-2-yl]-2,5-diphenyltetrazolium bromide). The cells were incubated with MTT for 45 min at 37° C., live cells oxidized MTT to blue dye precipitated in cytosol while dead cells remained colorless. Then removed media and solubilized the blue precipitate with 100 µl/well of 0.5% (w/v) SDS, 25 mM HCl, in 90% (v/v) isopropanol. The plates were vortexed and the intensity of the oxidized MTT read at 570 nm using the microplate reader. Another group of cells was challenged with the toxins for 48 hours in serum-free DMEM, then viability was determined by cytotoxicity assay with MTT as described above Cytotoxicity Assay in the Co-Culture Model We designed a co-culture model to mimic the in vivo condition to verify whether PA-L1 and PA-L2 specifically killed MMP expressing tumor cells, not MMP non-expressing cells. Vero, HT1080, A2058 and MDA-MB-231 cells were cultured into the different chambers of 8-chamber slide (Nalge Nunc International, Naperville, Ill.) to 80-100% of confluence. Then the cells were washed twice with serum-free DMEM, the chamber partition was removed, and the slide was put into a petri culture dish with serum free medium, so that the different cells were in the same culture environment. PA, PA-L1 or PA-L2 (300 ng/ml) each plus FP59 (50 ng/ml), or FP59 (50 ng/ml) alone were added to the cells and incubated to 48 hours. Then MTT (0.5 mg/ml) was added for 45 min at 37° C., the partition was remounted, the oxidized MTT was dissolved as described above to determine cell viability for each chamber.

Cell Binding and Processing Assay of WT-PA. PA-L1 and PA-L2

Binding and processing of WT-PA, PA-L1 and PA-L2 on the surface of Vero cells and HT1080 cells was assayed. Vero and HT1080 cells were grown in 24-well plate to 80-100% of confluence and washed twice with serum-free DMEM to remove residual FCS. Then the cells were incubated with 1000 ng/ml of WT-PA, PA-L1 and PA-L2, respectively, for different length of time (0, 10 min, 40 min, 120 min and 360 min) at 37° C. in serum-free DMEM. The cells were washed three times to remove unbound PA proteins. Cells were lysed in 100 µl/well modified RIPA lysis buffer (50 mM Tris-HCl, pH 7.4, 1% NP40, 0.25 Na-deoxycholate, 150 mM NaCl, 1 mM EDTA, 1 mM PMSF, 1 mg/ml each of aprotinin, leupeptin and pepstatin) on ice for 10 min. Equal amounts of protein from cell lysates were separated by PAGE using 10-20% gradient Tris-glycine gels (Novex, San Diego, Calif.). After transfer to nitrocellulose membranes, blocking was done with 5% non-fat milk. Western blotting used rabbit anti-PA polyclonal antibody (#5308). Blot was washed and incubated with an HRP-conjugated goat anti-rabbit antibody (sc-2004)

(Santa Cruz Biotechnology, Inc., Santa Cruz, Calif.) and was visualized by EL (PIERCE, Rockford, Ill.).

Construction and Transfection of MT1-MMP into COS-7 Cells

MT1-MMP cDNA was a generous gift of J. Windsor, AB. The pEGFPN1 (Clontech Laboratories, Inc., Palo Alto, Calif.) mammalian expression vector was used for fusing the C-terminus of MT1-MMP to the N-terminus of EGFP (red shifted variant of green fluorescent protein). The MT1-MMP coding sequence was isolated with Tth III and then filled in with Pfu and inserted into the SmaI site of pEGFPN1. COS-7 Cells ($2 \times 10^5$ per dish) were transfected with expression vectors (2 µg) by means of SuperFect (10 ml) (Qiagen). Cells were incubated for 3 h. with the DNA-SuperFect complex in the presence of serum and antibiotic containing medium. The complex containing medium was removed and cells grown in fresh serum containing medium for 48 h. Thereafter cells were grown in G418 (Life Technologies, Inc.) containing medium. Cells expressing the MT1-MMP/GFP fusion protein, named COSgMT1, were sorted from non-expressing cells by flowcytometry with a FACstar Plus (Becton Dickinson), excitation at 488 nm.

B. Results

Generation of PA Mutants Which can be Activated by MMPs

Crystal structure of PA showed that the furin cleavage site $RKKR_{167}$ is in the middle of a surface flexible, solvent exposed loop composed of aa 162 to 175 (Petosa, C., et al., Nature, 385:833-838 (1997)). Cleavage in this loop by furin-like proteases is essential to toxicity. To construct PA mutants specifically processed by MMPs, especially MMP-2 and MMP-9, instead of furin, the furin site $RKKR_{167}$ (SEQ ID NO:1) was replaced by MMP-2 and MMP-9 favorite sequences, GPLGMLSQ and GPLGLWAQ (SEQ ID NOS:2 and 3), respectively, resulting in two PA mutants, PA-L1 and PA-L2 (FIG. 1*a*). These two MMP substrate octapeptides were designed based on the studies of Netzel-Arneet et al (Netzel-Arnett, S., et al., *J Biol Chem,* 266:6747-6755 (1991); Netzel-Arnett, S., et al., *Biochemistry,* 32:6427-6432 (1993)), in which the sequence specificity of human MMP-2, MMP-9, matrilysin, MMP-1 and MMP-8 had been examined by measuring the rate of hydrolysis of over 50 synthetic oligopeptides. These two octapeptides are favorite substrates of MMP-2 and MMP-9, but also overlap to other MMP species (Netzel-Arnett, S., et al., *J Biol Chem,* 266:6747-6755 (1991); Netzel-Arnett, S., et al., *Biochemistry,* 32:6427-6432 (1993)). They are also potential substrates for MT1-MMP (Will, H., et al., *J Biol Chem,* 271:17119-17123 (1996)). PA-L1 and PA-L2 coding sequences were constructed by overlap PCR, cloned into *E. coli-Bacillus* shuttle vector pYS5, and efficiently expressed in non-virulent *Bacillus Anthracis* UM23C1-1. The expression products were secreted into the culture supernatants and reached to 20 to 50 mg/L. These two mutated PA proteins were roughly purified by ammonium sulfate precipitation, followed by mono Q chromatography. The purified mutated PA proteins PA-L1 and PA-L2 commiserated with WT-PA in SDS-PAGE, but migrated faster than WT-PA in native gel because of the four positively charged residues RKKR (SEQ ID NO:1) of the furin site were replaced into non-charged MMP octapeptides (data not shown).

To characterize WT-PA and these two PA mutants in susceptibility to proteases, they were subjected to the cleavage with soluble form furin, active form MMP-2 and MMP-9 in vitro. WT-PA was very sensitive to furin, but complete resistant to MMP-2 and MMP-9 (FIG. 1*b*). In contrast, PA-L1 and PA-L2 were completely resistant to furin, but got the new feature to be efficiently processed into two fragments, PA63 and PA20, by MMP-2 and MMP-9 (FIG. 1*c* and 1*d*). There was no apparent difference between the two PA mutants in respect to the processing patterns by furin, MMP-2 and MMP-9. However, it seemed PA-L1 and PA-L2 were processed more efficiently by MMP-2 than by MMP-9.

PA-L1 and PA-L2 Killed MMP Expressing Tumor Cells but not MMP Non-Expressing Cells To test the hypothesis that PA-L1 and PA-L2 only kill MMP expressing tumor cells, but not MMP non-expressing normal cells, three human tumor cell lines, fibrosarcoma HT1080, melanoma A2058 and breast cancer MDA-MB-231, and one non-tumor cell line Vero, were employed in cytotoxicity assay. Gelatin zymography showed that HT1080 expressed both MMP-2 and MMP-9, A2058 only expressed MMP-2, MDA-MB-231 only expressed MMP-9, in both conditioned serum-free media and cell extracts, reflecting the gelatinases expressed by these three tumor cell lines were secreted into the media and may also associated with the cell surface (FIG. 2). In contrast, Vero cells had very low background of MMP expression (FIG. 2).

Cytotoxicity of WT-PA and the PA mutants to these cells were performed onto 96-well plates. When cells grew to 80 to 100% confluence, different concentrations (from 0 to 1000 ng/ml) of WT-PA, PA-L1 and PA-L2 combined with FP59 (constant at 50 ng/ml) were separately added to the cells and challenged the cells for 6 hours and 48 hours. For the PA dependent cytotoxicity of FP59 relies on inhibition of initial protein synthesis by ribosylating EF-2, cytotoxicity was allowed to develop for 48 hours. The $EC_{50}$ (concentration needed to kill half of the cells) of PA and the PA mutants were summarized in Table 1. FIG. 3*a* showed MMP non-expressing Vero cells were quite resistant to PA-L1 and PA-L2, but very sensitive to wild-type PA with dose-dependent manner. However, the PA-L1 and PA-L2 nicked by MMP-2 in vitro efficiently killed Vero cells even with 6 hours toxin challenge in dose-dependent manner (FIG. 3*b*), demonstrating the non toxicity of PA-L1 and PA-L2 to Vero cells was due to Vero cells lack the ability of processing them into the active form PA63. We will show later (in FIG. 7) that WT-PA, PA-L1 and PA-L2 quickly bound to Vero cells, but only WT-PA could be processed by Vero cells to the active form PA63, while PA-L1 and PA-L2 not. In contrast to Vero cells, the two MMP expressing tumor cells, HT1080, A2058 and MDA-MB-231, were quite susceptible to WT-PA as well as PA-L1 and PA-L2 (FIGS. 4*a*, 4*b* and 4*c*), and the sensitivity to these PA mutants seemed directly correlated with the overall expression levels of MMPs of these tumor cells (FIG. 2).

TABLE 1

$EC_{50}$[a] (ng/ml) of wild type and mutated PA proteins (plus 50 ng/ml FP59) on target cells

| | Vero | HT1080 | A2058 |
|---|---|---|---|
| WT-PA | 5[b](6)[c] | 2.5 (5.5) | 2 (6) |
| PA-L1 | >>1000 (>>1000) | 2 (10) | 4 (20) |
| PA-L2 | >>1000 (>>1000) | 2 (10) | 7 (25) |
| Nicked[d] PA-L1 | 20 | | |
| Nicked[d] PA-L2 | 20 | | |
| | MDA-MB-231 | COS-7 | COSgMT1 |
| WT-PA | 1 (2) | 6 (15) | 20 (30) |
| PA-L1 | 3 (15) | >>1000 (>>1000) | 20 (40) |

TABLE 1-continued EC$_{50}$[a] (ng/ml) of wild type and mutated PA proteins (plus 50 ng/ml FP59) on target cells

| | | | |
|---|---|---|---|
| PA-L2 | 4 (30) | >>1000 (>>1000) | 20 (20) |
| Nicked[d] PA-L1 | | | |
| Nicked[d] PA-L2 | | | |

[a]EC$_{50}$ is the concentration of toxin required to kill half of the cells compared with untreated controls. EC$_{50}$ values are interpolated from FIG. 3, 4 and 8.
[b]EC$_{50}$ value for 48 hours toxin treatment
[c]Value in parenthesis is EC50 for 6 hours toxin treatment
[d]Nicked by MMP-2

Figure 5:
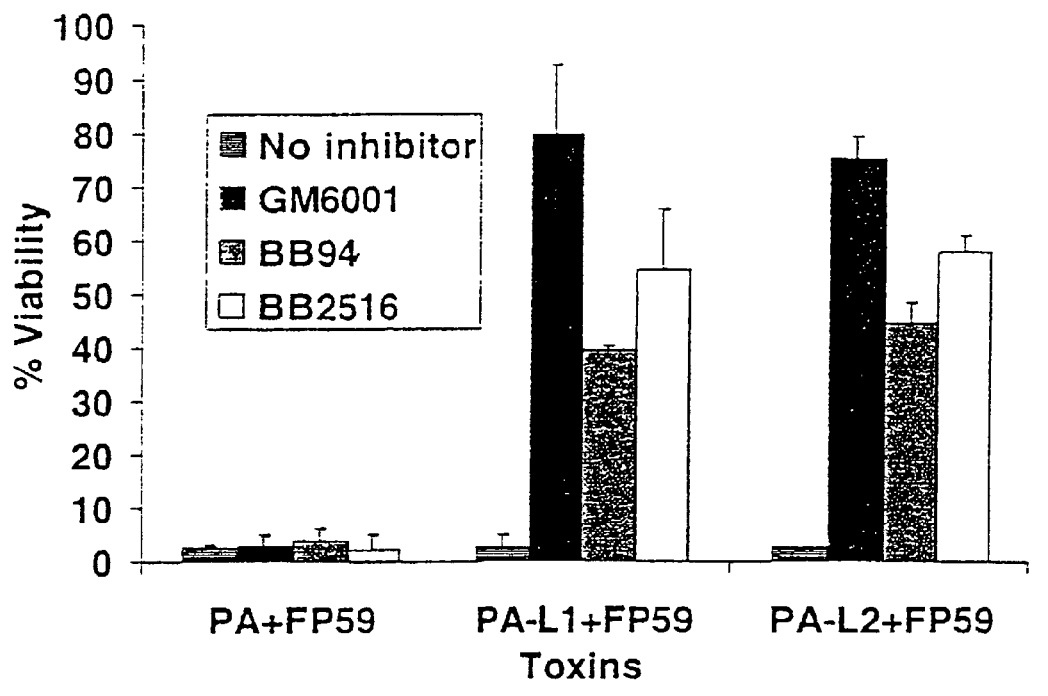

To further demonstrate the cytotoxicity of the PA mutants to the tumor cells was dependent on MMP activity expressed by the target cells, we characterized the effects of the well described MMP inhibitors, BB94 (Batimastat), BB-2516 (Marimastat)), and GM6001, on cytotoxicity of WT-PA, PA-L1 and PA-L2 to HT1080 cells. All these MMP inhibitors, especially GM6001, conferred clear protection to HT1080 cells against the challenge with PA-L1 and PA-L2 plus FP59, but did not protect the cells against WT-PA plus FP59 (FIG. 5). Thus, killing the tumor cells by PA-L1 and PA-L2 was really dependent on MMP activity expressed by the target cells.

Figure 6:
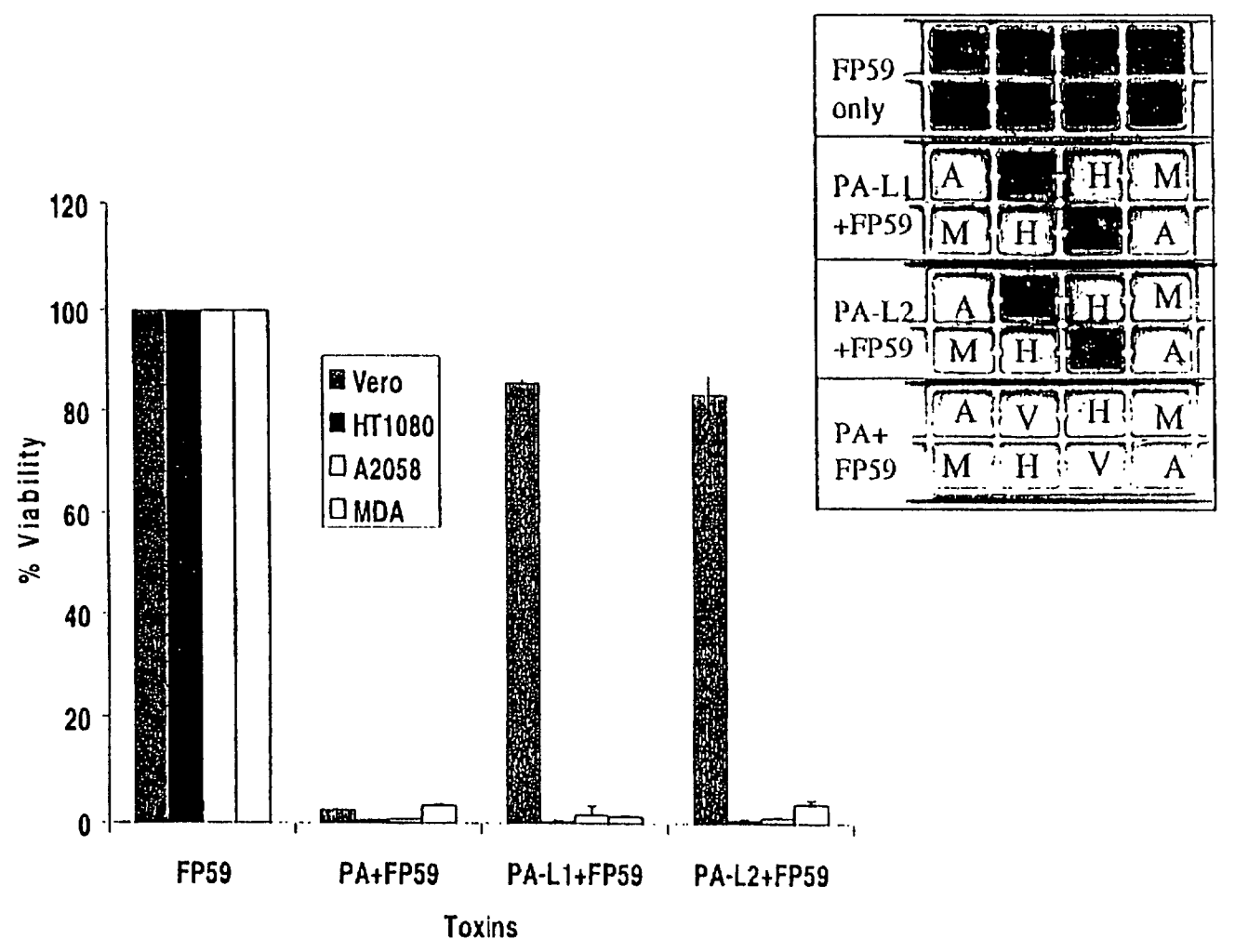
Figure 7:
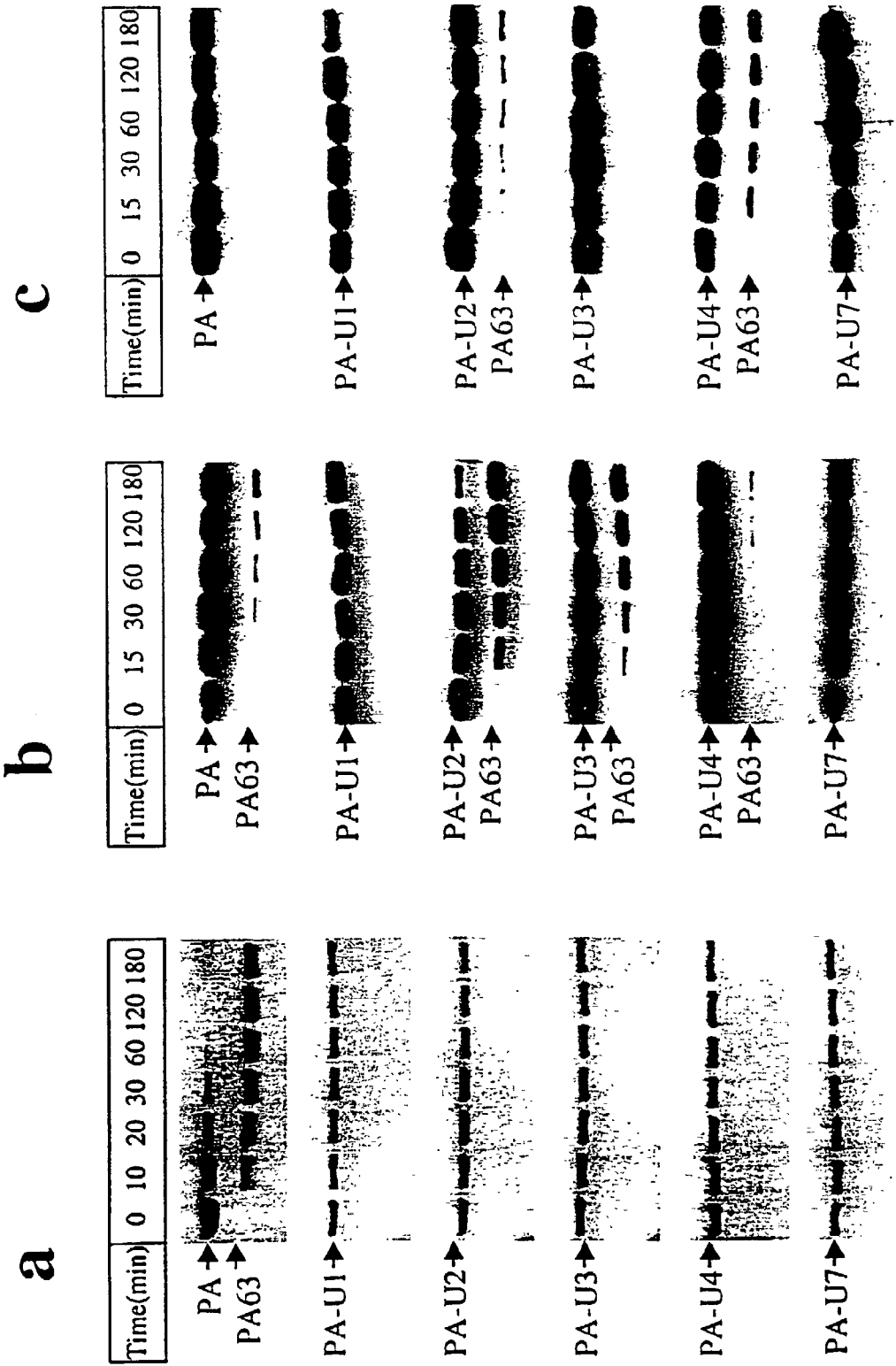
FIG. 7. Binding and activation processing of PA, PA-L1 and PA-L2 on the cell surface of Vero (A) and HT1080 (B) cells. As described in Materials and Methods, Vero and HT1080 cells were cultured in 24-well plates to 80-100% of confluence, washed and changed serum-free media. Then PA, PA-L1 and PA-L2 were added to the cells with a final concentration of 1000 ng/ml, incubated for different times (0, 10 min, 40 min, 120 min and 360 min). The cell lysates were prepared for western blotting analysis using rabbit anti-PA polyclonal antibody (#5308) to check the processing status of PA and PA mutants.

PA-L1 and PA-L2 Specifically Killed MMP Expressing Tumor Cells in a Co-Culture Model We designed a co-culture model to mimic the in vivo condition to verify whether PA-L1 and PA-L2 specifically kill MMP expressing tumor cells, not MMP non-expressing cells. Vero, HT1080, MDA-MB-231 and A2058 cells were cultured into the different chambers of 8-chamber slides. When the cells reached confluence, the chamber partition was removed and the slide was put into a petri culture dish with serum free medium, so that the different cells were in the same culture environment. PA, PA-L1 or PA-L2 (300 ng/ml) plus FP59 (50 ng/ml), or FP59 (50 ng/ml) alone were separately added to the cells and incubated for 48 hours for cytotoxicity assay as described in Materials and Methods. The result showed WT-PA unselectively killed all cells, meanwhile PA-L1 and PA-L2 only killed HT1080, MDA-MB-231 and A2058 cells, but did not hurt MMP non-expressing Vero cells (FIG. 5). This result defined the relative contributions of membrane-associated versus soluble MMPs, indicated the activation processing of the PA mutants mainly happened on the surface of the tumor cells instead of in the supernatant. Binding and processing of WT-PA, PA-L1 and PA-L2 on the surface of MMP non-expressing Vero cells and MMP expressing HT1080 cells were also directly assessed. Vero and HT1080 cells were incubated with WT-PA, PA-L1 and PA-L2 for 0, 10 min, 40 min, 120 min and 360 min at 37° C., respectively. Then the cells were washed and cell lysates were prepared for western blotting analysis to check the transformation of WT-PA and PA mutants to the active form PA63. The data showed WT-PA, PA-L1 and PA-L2 could be detected in the Vero and HT1080 cell lysates as soon as 10 min after incubation, demonstrating WT-PA and PA mutants could quickly bound to the cell surface (FIG. 7a, 7b). WT-PA was processed by both of these two cell lines. In contrast, PA-L1 and PA-L2 were only processed by MMP expressing HT1080 cells but not MMP non-expressing Vero cells (FIG. 7a, 7b), being consistent with the previous results that PA-L1 and PA-L2 could only be processed by MMPs (FIGS. 1b and 1c) and selectively killed MMP-expressing tumor cells (FIG. 6). Though HT1080 cells processed WT-PA, PA-L1 and PA-L2, but the results showed the cells processed WT-PA more efficiently than PA-L1 and PA-L2 (FIG. 7b), reflecting the activity of furin or furin-like proteases was higher than that of MMPs on the cell surface.

We also analyzed the processing status of PA-L1 and PA-L2 in the culture supernatants of HT-1080 cells, and could not detect their active form PA63 in the overnight culture supernatants, but with time increasing the randomly breakdown products showed up (data not shown).

MT1-MMP Played a Role in Activation of PA-L1 and PA-L2

Zymographic analysis showed COS-7 cells expressed very negligible amount gelatinases (FIG. 8a insert). Thus, just as expected, COS-7 cells were resistant to PA-L1 and PA-L2 plus FP59, but susceptible to WT-PA plus FP59 (FIG. 8a). To examine the role of MT1-MMP in activation of PA-L1 and PA-L2, encoding sequence of MT1-MMP was transfected into COS-7 cells, resulting in a stable transfectant COSgMT1 in which expression of MT1-MMP was detected by western blotting (FIG. 8b insert). In contrast to COS-7 cells, COS-gMT1 became very sensitive to PA-L1 and PA-L2 (FIG. 8b), indicating MT1-MMP played a role in activation of these PA mutants, either by directly processing the cell bound PA mutants, or by indirect way that activated pro-MMP-2 or other MMPs first, which in turn processed PA mutants to their active form PA$_{63}$. It seemed unlikely the later one, for COS-7 cells expressed negligible amount of MMPs.

Example II

Construction of Mutant PA with Matrix Metalloproteinase Cleavage Sites

Mutant PA proteins were constructed and tested as described in Example I, substituting one of the following plasminogen activator cleavage sites of Table 2 for the MMP cleavage sites described above. Phage display libraries were used to identify sequences having specificity for a particular protease (see, e.g., Coombs et al., J. Biol. Chem. 273:4323-4328 (1998); Ke et al., J. Biol. Chem. 272:20456-20462 (1997); Ke et al., J. Biol. Chem. 272:16603-16609 (1997)). These libraries can be used by one of skill in the art to select sequences specifically recognized by MPP and plasminogen activator proteases.

TABLE 2 u-TP and t-PA cleavage sites

| Substrate sequence | SEQ ID NO: | u-PA Kcat/Km | t-PA Kcat/Km | a-PA:t-PA selectivity |
|---|---|---|---|---|
| PCPGRVVGG | 4 | 0.88 | 0.29 | 3.0 |
| PGSGRSA | 5 | 1200 | 60 | 20 |
| PGSGKSA | 6 | 193 | 1.6 | 121 |
| PQRGRSA | 7 | 45 | 850 | 0.005 |

Example III

Construction of Mutant PA with Plasminogen Activator Cleavage Sites

A. Materials

Enzymes for DNA manipulation and modification were purchased from New England Biolabs (Beverly, Mass.). FP59 and a soluble form of furin were prepared in our laboratory as described (Gordon, V. M., et al., Infect. Immun., 65:4130-4134 (1997)). Rabbit anti-PA polyclonal antibody (#5308) was made in our laboratory. Pro-uPA (single-chain uPA, #107), uPA (#124), tPA (#116), human urokinase amino-terminal fragment (ATF) (#146), human glu-plasminogen (#410), human PAI-1 (#1094), human plasmin (#421), monoclonal antibody against human uPA B-chain (#394) were purchased from America Diagnostica inc (Greenwich, Conn.). Goat polyclonal antibody against human t-PA (sc-5241) was purchased from Santa Cruz Biotechnology, Inc. (Santa Cruz, Calif.). UPAR monoclonal antibody R3 was a gift Construction of Mutated PA Proteins A modified overlap PCR method was used to construct the mutated PA proteins in which the furin site is replaced by the uPA and tPA physiological substrate sequence PCPGRV-VGG (SEQ ID NO:4) in PA-U1, uPA favorite sequences PGSGRSA (SEQ ID NO:5) and PGSGKSA (SEQ ID NO:6) in PA-U2 and PA-U3, respectively, tPA favorite sequence PQRGRSA (SEQ ID NO:7) in PA-U4. The PA expression plasmid pYS5 (Singh, Y., et al., *J Biol Chem,* 264:19103-19107 (1989)) was used as template. A 5' primer F, AAAGGAGAACGTATATGA (SEQ ID NO:8) (Shine-Dalgarno and start codons are underlined), and the phosphorylated reverse primer R1, pTGGTGAGTTCGA AGATTTTTGTTTTAATTCTGG (SEQ ID NO:13) (the first three nucleotides encodes P, the others anneal to the sequence corresponding to $P_{154}$-$S_{163}$), were used to amplify a fragment designated "N". A mutagenic phosphorylated primer H1, pTGTCCAGGAAG AGTAGTTGGAGGAAGTACAAGTGCTGGACCTACGGTTCCAG (SEQ ID NO: 14), encoding CPGRVVGG (SEQ ID NO:15) and $S_{168}$-$P_{176}$, and reverse primer R2, ACGTTTATCTCTTATTAAAAT (SEQ ID NO:11), annealing to the sequence encoding $I_{589}$-$R_{595}$, were used to amplify a mutagenic fragment "M1". A phosphorylated mutagenic primer H2, pGGAAGTGGAAGATCAGCAAGTACAAGTGCTGGACCTAC GGTTCCAG (SEQ ID NO:16), encoding GSGRSA (SEQ ID NO:17) and $S_{168}$-$P_{176}$, and reverse primer R2 were used to amplify a mutagenic fragment "M2". A phosphorylated mutagenic primer H3, pGGAAGTGGAAAATCAGCAAGTACAAGTGCTGGACCTA CGGTTCCAG (SEQ ID NO:18), encoding GSGKSA (SEQ ID NO:19) and $S_{168}$-$P_{176}$, and reverse primer R2, were used to amplify a mutagenic fragment "M3". A phosphorylated mutagenic primer H4, pCAGAGAGGAAGATCAGCAAGTACAAGTG CTGGACCTACGGTTCCAG (SEQ ID NO:20), encoding QRGRSA (SEQ ID NO:21) and $S_{168}$-$P_{176}$, and reverse primer R2, were used to amplify a mutagenic fragment "M4". Primers F and R2 were used to amplify the ligated products of N+M1, N+M2, N+M3, and N+M4, respectively, resulting in the mutagenized fragments U1, U2, U3, and U4 in which the coding sequence for the furin site ($RKKR_{167}$; SEQ ID NO:1) is replaced by uPA or tPA substrate. The HindIII/PstI digests of U1, U2, U3, and U4 were cloned between the HindIII and PstI sites of pYS5. The resulting expression plasmids were named pYS-PA-U1, pYS-PA-U2, pYS-PA-U3, and pYS-PA-U4, and their expression products, the mutated PA proteins, were accordingly named PA-U1, PA-U2, PA-U3, and PA-U4. One expression plasmid encoded a mutant in which $RKKR_{167}$ (SEQ ID NO:1) is replaced by PGG, expected not to be cleaved by any protease. Its expression plasmid and expression product were named pYS-PA-U7 and PA-U7, respectively.

Expression and Purification of PA and Mutated PA Proteins

To express PA, PA-U1, PA-U2, PA-U3, PA-U4, and PA-U7, the expression plasmids pYS5, pYS-PA-U1, pYS-PA-U2, pYS-PA-U3, pYS-PA-U4, and pYS-PA-U7, were transformed into non-virulent strain *B. anthracis* UM23C1-1 and grown in FA medium (Singh, Y., et al., *J. Biol. Chem.,* 264:19103-19107 (1989)) with 20 μg/ml of kanamycin for 16 h at 37° C. The expression products were secreted into the culture supernatants. The mutated PA proteins were concentrated and purified by chromatography on a MonoQ column (Amersham Pharmacia Biotech, Piscataway, N.J.), as described previously (Varughese, M., et al., *Mol. Med.,* 4:87-95 (1998)).

In Vitro Cleavage of PA and Mutated PA Proteins by uPA, tPA, and Furin

Reaction mixtures of 50 μl containing 5 μg of the PA proteins were incubated at 37° C. with 5 μl of soluble furin or 0.5 μg of uPA or tPA. Furin cleavage was done in 25 mM HEPES, pH 7.4, 150 mM NaCl, 0.2 mM EDTA, 0.2 mM EGTA, 100 μg/ml ovalbumin, 1.0 mM $CaCl_2$, and 1.0 mM $MgCl_2$. Aliquots (5 μl) withdrawn at intervals were separated by polyacrylamide gel electrophoresis (PAGE) using 10-20% gradient Tris-glycine gel (Novex, San Diego, Calif.) and visualized by Commassie staining.

Cleavage with uPA or tPA was done in 150 mM NaCl, 10 mM Tris-HCl (pH 7.5). Aliquots withdrawn at intervals were diluted 1:1000 and separated by PAGE using 10-20% gradient Tris-glycine gel (Novex, San Diego, Calif.) and electroblotted to a nitrocellulose membrane (Novex, San Diego, Calif.). Cleavage was assessed by Western blotting with a rabbit anti-PA antibody. Membranes were blocked with 5% (w/v) non-fat milk, incubated sequentially with rabbit anti-PA polyclonal antibody (#5308) and horse radish peroxidase-conjugated goat anti-rabbit antibody (sc-2004, Santa Cruz Biotechnology, Inc., Santa Cruz, Calif.), and visualized by ECL (Pierce, Rockford, Ill.).

Cells and Culture Medium

Vero cells, human cervix adenocarcinoma Hela cells, human melanoma A2058 cells, human melanoma Bowes cells, and human fibrosarcoma HT1080 cells were obtained from American Type Culture Collection (Manassas, Va.). All cells were grown in Dulbecco's Minimal Essential Medium (DMEM) with 0.45% glucose, 10% fetal bovine serum, 2 mM glutamine, and 50 pg/ml gentamicin. Human primary vascular endothelial cells were obtained and cultured according to standard methodology. Cells were maintained at 37° C. in a 5% $CO_2$ environment.

Binding and Processing of Pro-PA by Cultured Cells

Vero cells, Hela cells, A2058 cells, and Bowes cells were cultured in 24-well plate to confluence, washed and incubated in serum-free media with 1 μg/ml of pro-uPA and 1 μg/ml of glu-plasminogen for 1 h, then the cell lysates were prepared for Western blotting analysis with monoclonal antibody against uPA B-chain (#394).

Cytotoxicity Assay with MTT

Cells were seeded into 96-well plates at approximately 25% confluence. The next day, cells were washed twice with serum-free DMEM to remove residual serum. Serial dilutions of PA, mutated PA proteins (0 to 1000 ng/ml) combined with FP59 (50 ng/ml) in serum-free DMEM (If targeting urokinase plasminogen activation system, 100 ng/ml pro-uPA and 1 μg/ml of glu-plasminogen were added) to the cells to give a total volume of 200 μl/well. In some experiments, PAI-1 was added 30 min prior to toxin addition. Cells was incubated with the toxins for 6 h, after which the medium was replaced with fresh DMEM supplemented with 10% FCS. Cell viability was then assayed by adding 50 μl of 2.5 mg/ml MTT (3-[4,5-dimethylthiazol-2-yl]-2,5-diphenyltetrazolium bromide). The cells were incubated with MTT for 45 min at 37° C., the medium was removed, and the blue pigment produced by viable cells was solubilized with 100 μl/well of 0.5% (w/v) SDS, 25 mM HCl, in 90% (v/v) isopropanol. The plates were vortexed and the oxidized MTT was measured as $A_{570}$ using a microplate reader.

Binding and Processing of PA and PA-U2 by Cultured Cells Cells were grown in 24-well plates confluence and washed twice with serum-free DMEM to remove residual serum. Then the cells were incubated with 1 µg/ml of PA and PA-U2 at 37° C. in serum-free DMEM containing 100 ng/ml of pro-uPA and 1 µg/ml of glu-plasminogen for different lengths of time. When PAI-1 was tested, it was incubated with cells for 30 min prior to the addition of PA proteins. The cells were washed five times to remove unbound PA proteins. Cells were lysed in 100 µl/well modified RIPA lysis buffer (50 mM Tris-HCl, pH 7.4, 1% NP40, 0.25% Na-deoxycholate, 150 mM NaCl, 1 mM EDTA, 1 mM phenylmethyl sulfonyl fluoride, 1 µg/ml each of aprotinin, leupeptin and pepstatin) on ice for 10 min. Equal amounts of protein from cell lysates were separated by PAGE using 10-20% gradient Tris-glycine gels (Novex, San Diego, Calif.). Western blotting to detect PA and its cleavage products was performed as described above.

Cytotoxicity Assay in a Co-Culture System

A co-culture model was designed to mimic the in vivo condition to verify whether PA-U2 kill uPAR-overexpressing tumor cells while not affecting uPAR non-expressing cells. Vero, Hela cells were cultured in separate chambers of 8-chamber slides (Nalge Nunc International, Naperville, Ill.) to 80-100% confluence. The cells were washed twice with serum-free DMEM, the chamber partition was removed, and the slide was put into a culture dish with serum-free medium containing 100 ng/ml pro-uPA and 1 µg/ml of Glu-plasminogen, so that all the cells were bathed in the same medium. PA and PA-U2 (300 ng/ml) and FP59 (50 ng/ml) were added individually or in combination and cells were exposed for 48 h. Then MTT (0.5 mg/ml) was added for 45 min at 37° C., the partitions were remounted, and the oxidized MTT in each chamber was dissolved as described above to determine the viability of each cell type. The cell lysates from different chambers were also prepared for Western blotting to detect PA proteins and their cleavage product PA63 species.

B. Results

Directing uPA or tPA Sequence-Specific Proteolysis to Anthrax PA

The crystal structure of PA shows that the furin site, $RKKR_{167}$ (SEQ ID NO: 1), is in a surface-exposed, flexible loop composed of aa 162 to 175 (Petosa, C., et al., *Nature*, 385:833-838 (1997)). Cleavage in this loop by furin or furin-like proteases is essential to toxicity. Mutated PA proteins were constructed in which the furin-sensitive sequence $RKKR_{167}$ (SEQ ID NO:1) is replaced by uPA or tPA substrate sequences. In mutated PA protein PA-U1, PCPGRVVGG (SEQ ID NO:4), a peptide from P5 to P4' in the physiological substrate plasminogen, was used to replace $RKKR_{167}$ (SEQ ID NO:1). In PA-U2, $RKKR_{167}$ (SEQ ID NO:1) was replaced by a peptide, PGSGRSA (SEQ ID NO:5), containing the consensus sequence SGRSA (SEQ ID NO:22) from P3 to P2', which was recently identified as the minimized best substrate for uPA (Ke, S. H., et al., *J. Biol. Chem.*, 272:20456-20462 (1997)). Because the peptide SGRSA (SEQ ID NO:22) is cleaved 1363-fold times more efficiently than a control peptide containing the physiological cleavage site present in plasminogen by uPA, and exhibits a uPA/tPA selectivity of 20 (Ke, S. H., et al., *J. Biol. Chem.*, 272:20456-20462 (1997)), PA-U2 was expected to be a favorite substrate of uPA. uPA/tPA selectivity of the peptide SGRSA (SEQ ID NO:22) can be further enhanced by placement of lysine in the P1 position (Ke, S. H., et al., *J. Biol. Chem.*, 272:20456-20462 (1997)), thus, the peptide PGSGKSA (SEQ ID NO:6), which exhibits a uPA/tPA selectivity of 121 (Ke, S. H., et al., *J. Biol. Chem.*, 272:20456-20462 (1997)), was used to replace $RKKR_{167}$ (SEQ ID NO:1) to construct a mutated PA protein, PA-U3, with even higher uPA selective activity than PA-U2. The investigation showed P3 and P4 residues were the primary determinants of the ability of a substrate to discriminate between tPA and uPA, and mutation of both P4 glycine and P3 serine of the most labile uPA substrate (GSGRSA; SEQ ID NO:17) to glutamine and arginine, respectively, decreased the uPA/tPA selectivity by a factor of 1200 and actually converted the peptide into a tPA-selective substrate (Ke, S. H., et al., *J. Biol. Chem.*, 272:20456-20462 (1997)). Based on this study, a mutated PA protein, PA-U4, was constructed. PA-U4 is expected to be a tPA favorite substrate, in which the peptide PQRGRSA (SEQ ID NO:7) was used to replace $RKKR_{167}$ (SEQ ID NO:1). A mutated PA protein PA-U7, was also constructed in which $RKKR_{167}$ (SEQ ID NO:1) was replaced by random sequence PGG, expected not to be cleaved by any known proteases, was used a control protein in this study. The designations of the mutated PA proteins along with the expected properties were summarized in Table 3.

Plasmids encoding these mutated PA proteins were constructed by a modified overlap PCR method, cloned into the *E. coli*-Bacillus shuttle vector pYS5, and efficiently expressed in *B. anthracis* UM23C1-1. The expression products were secreted into the culture supernatants at 20-50 mg/L. The mutated PA proteins were concentrated and purified by MonoQ chromatography to one prominent band at the expected molecular mass of 83 kDa which co-migrated with PA in SDS-PAGE. Thus, using a production protocol that is now standard for PA, these mutated PA proteins could be expressed and purified easily, in high yield and purity.

To verify that the mutated PA proteins had the expected susceptibility to proteases, they were subjected to cleavage with a soluble form of furin, uPA and tPA. As expected, these mutated PA proteins, had completely lost the susceptibility to furin. In contrast, wild-type PA was very sensitive to furin and processed to the active form PA63 (FIG. 9a). The cleavage profiles of these mutated PA proteins by uPA and tPA were quite consistent with that obtained from the peptide substrates (FIG. 9b, 9c). PA-U2 was efficiently cleaved by uPA, which was followed by PA-U3. PA-U3 could only be cleaved by uPA, but not tPA, showing high uPA specificity. However, PA-U2 was also slightly cleaved by tPA, being a week substrate for tPA. In contrast, PA-U4 was a very week substrate for uPA, but a good substrate for tPA. PA-U7 as well as PA-U1 were both completely resistant to uPA and tPA. PA was completely resistant to tPA, but was a week substrate for uPA (FIG. 9b). These results implicated PA-U2 and PA-U3 which can be selectively activated by uPA may be useful to target tumor cell surface-associated plasminogen activation system for tumor therapy, while PA-U4 may be toxic to tPA expressing cells which usually occurred in neuroblastomas.

PA-U2 and PA-U3 Selectively Kill Tumor Cells by Targeting Tumor Cell Surface-Associated Plasminogen Activation System UPAR is typically overexpressed in tumor cell lines and tumor tissues, and is the central part of cell surface-associated plasminogen activation system which is essential to tumor invasion and metastasis. To test the hypothesis that PA-U2 and PA-U3 would preferentially kill uPAR-overexpressing tumor cells, cytotoxicity assays were performed with three human tumor cell lines: cervix adenocarcinoma Hela, melanoma A2058, and melanoma Bowes. A non-tumor monkey cell line, Vero, was used as control.

Figure 10:
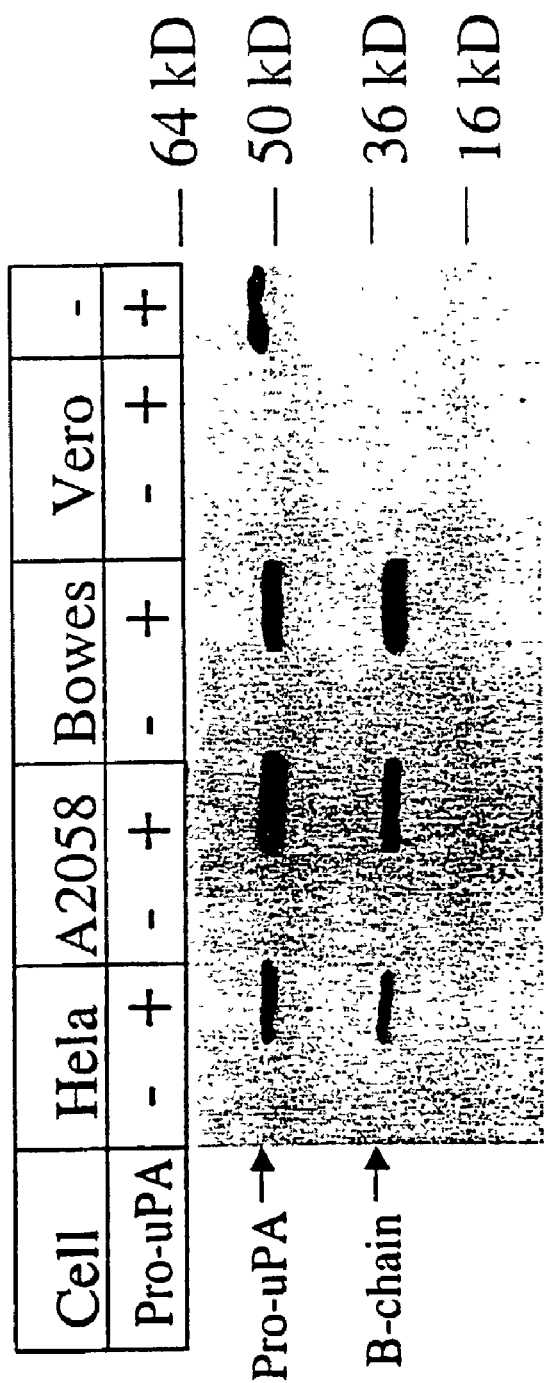

The expression of uPAR by these three tumor cell lines but not by Vero cells was evidenced by binding and processing of pro-uPA to the active form two-chain uPA by these three tumor cells but not by Vero cells. FIG. 10 showed that after 1 h incubation with the cells, pro-uPA and the processed form uPA B-chain could be detected from these three tumor cell lysates but not from Vero cells.

Figure 11:
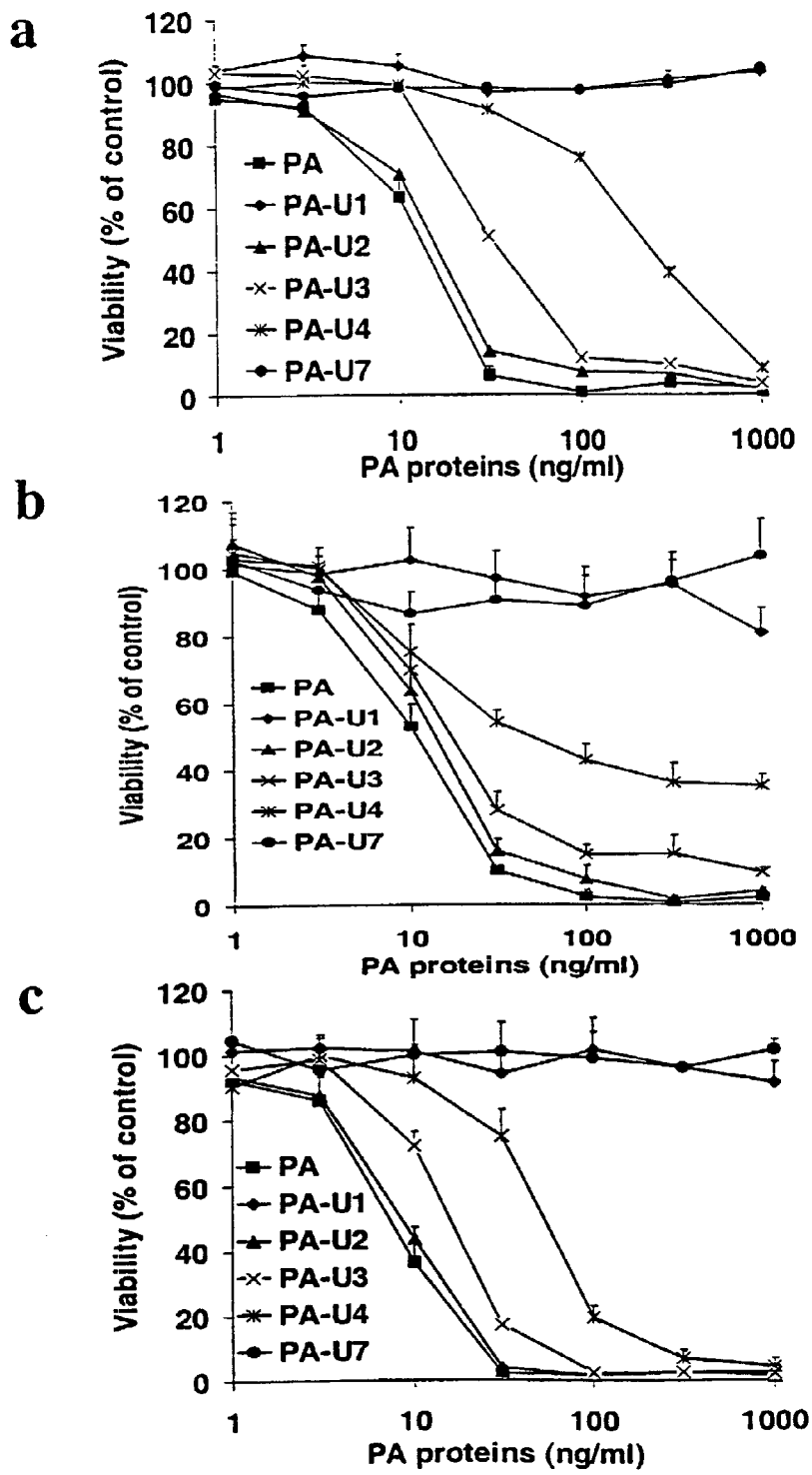
Figure 12:
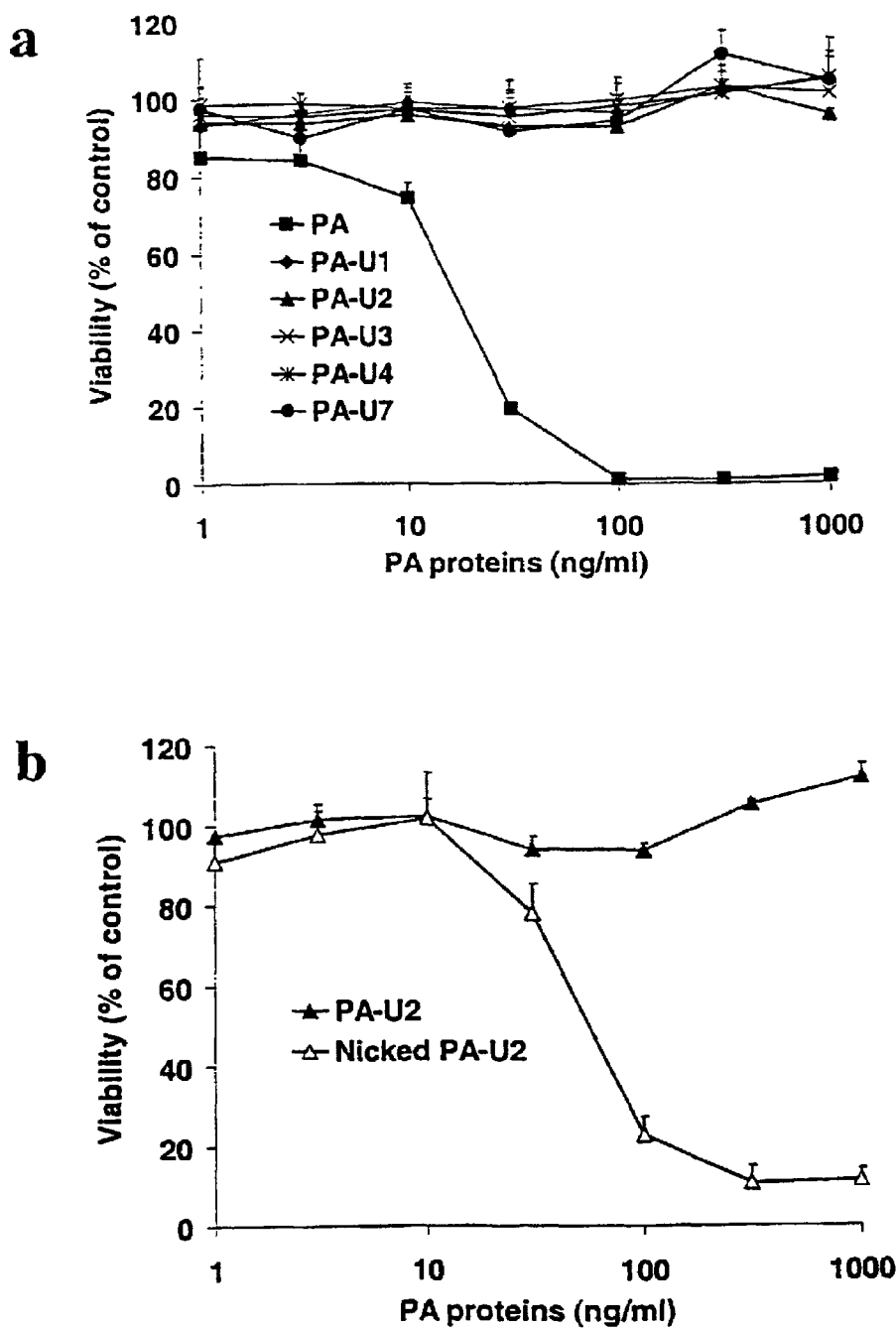

Cytotoxicity of PA and the mutated PA proteins to these cells was measured in 96-well plates. In tumor tissues, tumor cells typically overexpress uPAR, while tumor stromal cells express pro-uPA which binds and thereby is activated on the tumor cell surface, therefore in the cytotoxicity assay 100 ng/ml of pro-uPA was added to the tumor cells to mimic the role of tumor stromal cells in vivo. In addition, plasminogen is an important component of plasminogen activation system, and present at high concentration (1.5-2.0 µM) in plasma and interstitial fluids, representing potential plentiful source of plasmin activity. Therefore. 1 µg/ml of glu-plasminogen was also added in the cytotoxicity assay. PA and the mutated PA proteins combined with FP59 were incubated with cells for 6 h, and the viability was measured after 48 h. The $EC_{50}$ values (concentrations needed to kill half of the cells) for PA and the mutated PA proteins are summarized in Table 4. The three uPAR-expressing tumor cells, Hela, A2058, and Bowes were very susceptible to PA as well as to PA-U2 and PA-U3, and less susceptible to PA-U4 (FIG. 11a, b, c). In contrast, these tumor cells were completely resistant to PA-U1 and PA-U7 (FIG. 11a, b, c). The order of the cytotoxicity of mutated PA proteins to these tumor cells: PA-U2>PA-U3>PA-U4>>PA-U1, PA-U7, was well correlated with the uPA cleavage profile showed in FIG. 9b. In contrast to the tumor cells, the uPAR non-expressing Vero cells were completely resistant to all the mutated PA proteins, but sensitive to PA in a dose-dependent manner (FIG. 12a). However, PA-U2 that was first nicked by uPA in vitro efficiently killed Vero cells (FIG. 11b). This demonstrated that the resistance of Vero cells to PA-U2 was due to the inability of the cells to proteolytically activate the mutated PA proteins.

Binding and proteolytically processing of PA and PA-U2 on cell surface were also assessed. Vero and Hela cells were incubated with PA and PA-U2 for various length of times. After that the cell lysates were prepared and examined by Western blotting to detect binding and processing status of the PA proteins to the active PA63 species. PA was processed by both cell types, and this could not be inhibited by PAI-1 (FIG. 13a, b). In contrast, PA-U2 was processed by Hela cells but not by Vero cells, and this could be completely blocked by PAI-1 (FIG. 13a, b), demonstrating the cleavage of PA-U2 on Hela cell surface was due to uPA activated on the surface. Although Hela cells proteolytically processed PA as well as PA-U2, the later was cleaved slower apparently due to its cleavage was secondary to pro-uPA activation (FIG. 13b).

Figure 14:
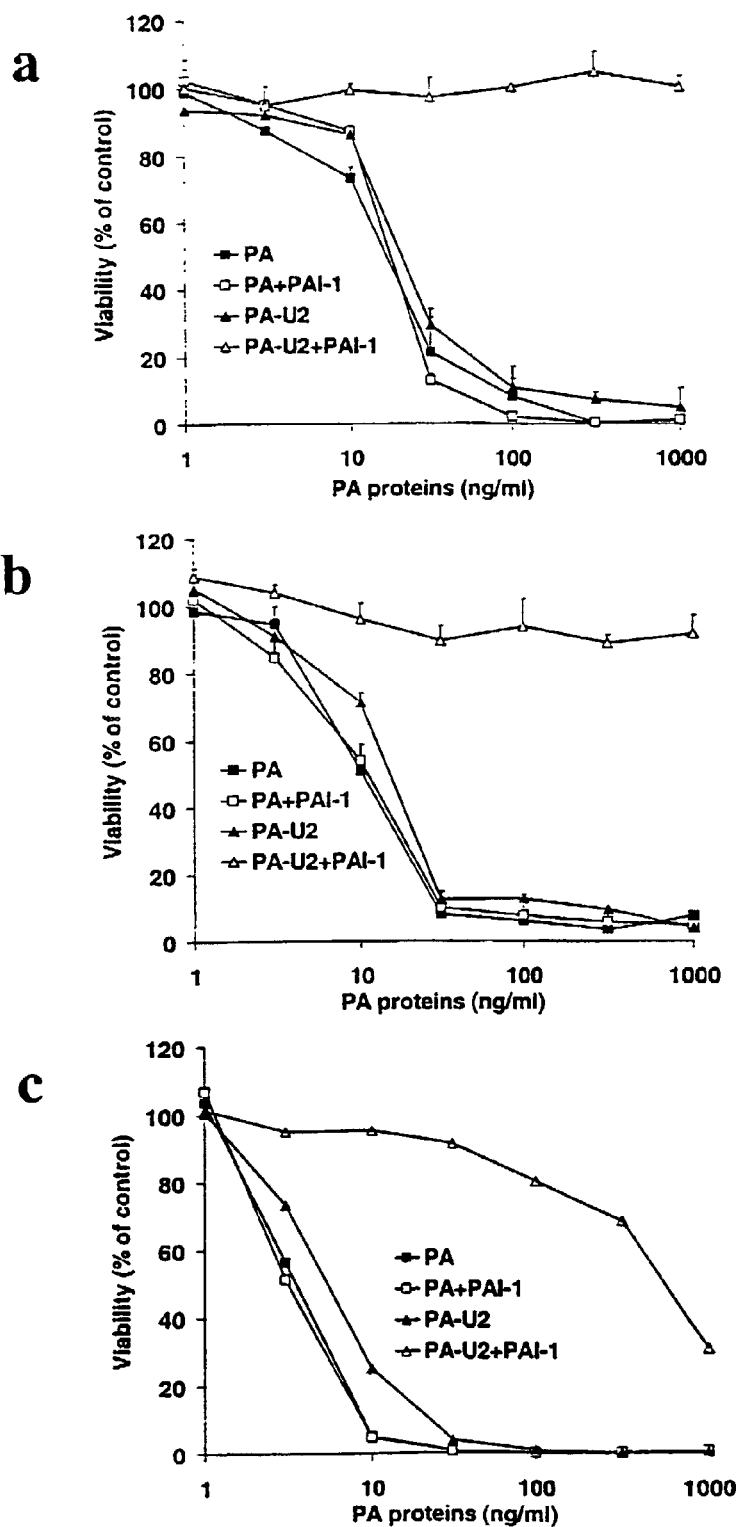
Figure 15:
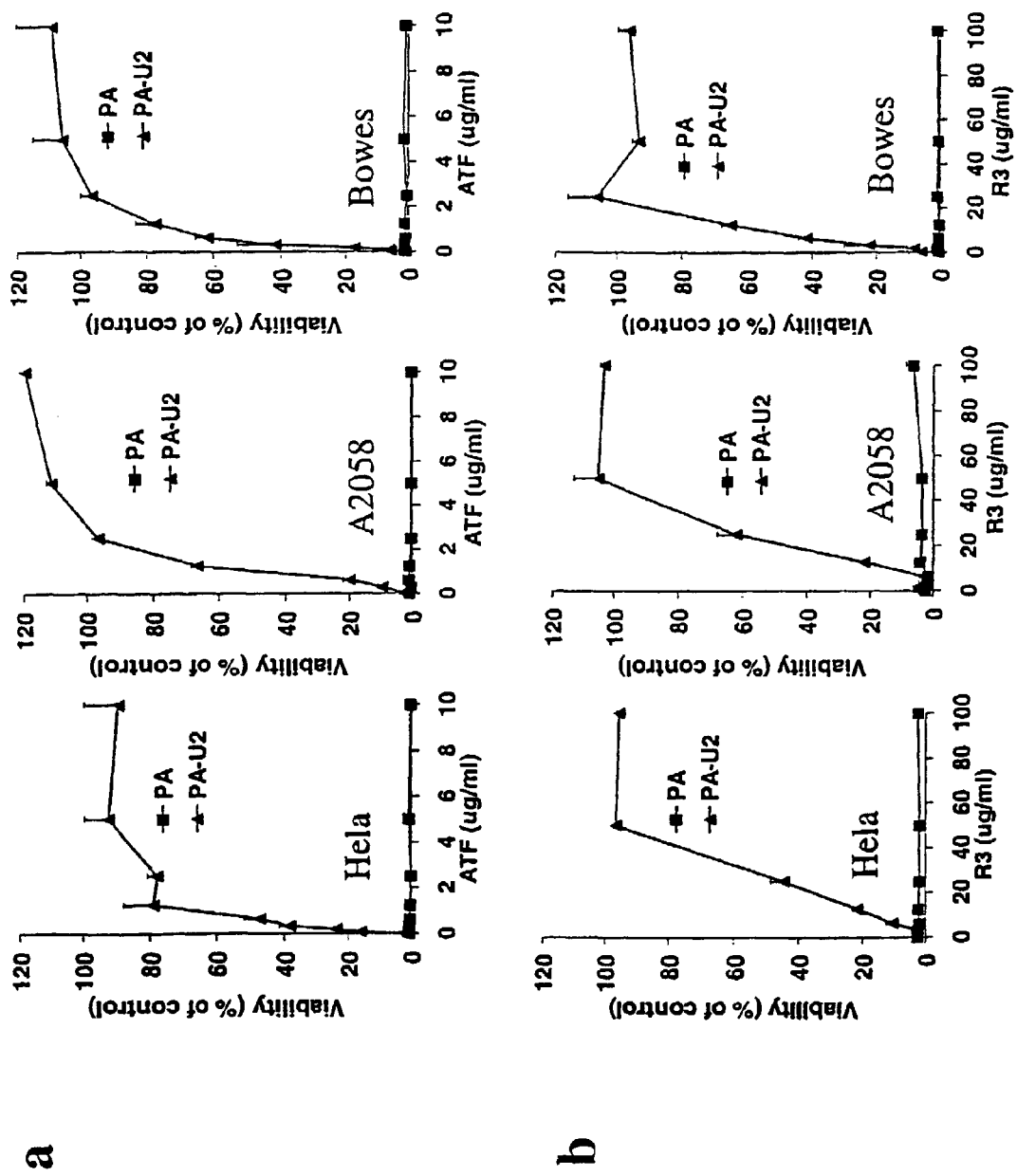

To further demonstrate that the cytotoxicity of the mutated PA proteins for tumor cells was dependent on the tumor cell surface-associated plasminogen activation system, the effects of the specific inhibitor and blockers of the system were characterized. PAI-1 conferred strong protections to all these three tumor cells against challenge with PA-U2 plus FP59, but did not protect the cells from PA plus FP59 (FIG. 14a, b, c). ATF, the animo-terminal fragment and uPAR binding domain of uPA, which competes the binding site on uPAR with pro-uPA, protected all three tumor cells from PA-U2 plus FP59 with dose-dependent manner (FIG. 15a). Similarly, UPAR blocking monoclonal antibody R3 which specifically interferes the binding between pro-uPA and uPAR, also protected the tumor cells in all three cases from PA-U2 plus FP59 (FIG. 15b). These results demonstrated killing of these tumor cells by PA-U2 was dependent on tumor cell surface-associated plasminogen activation system.

PA-U2 Retained Selectivity for uPAR-Expressing Cells in a Co-Culture Model

Figure 16:
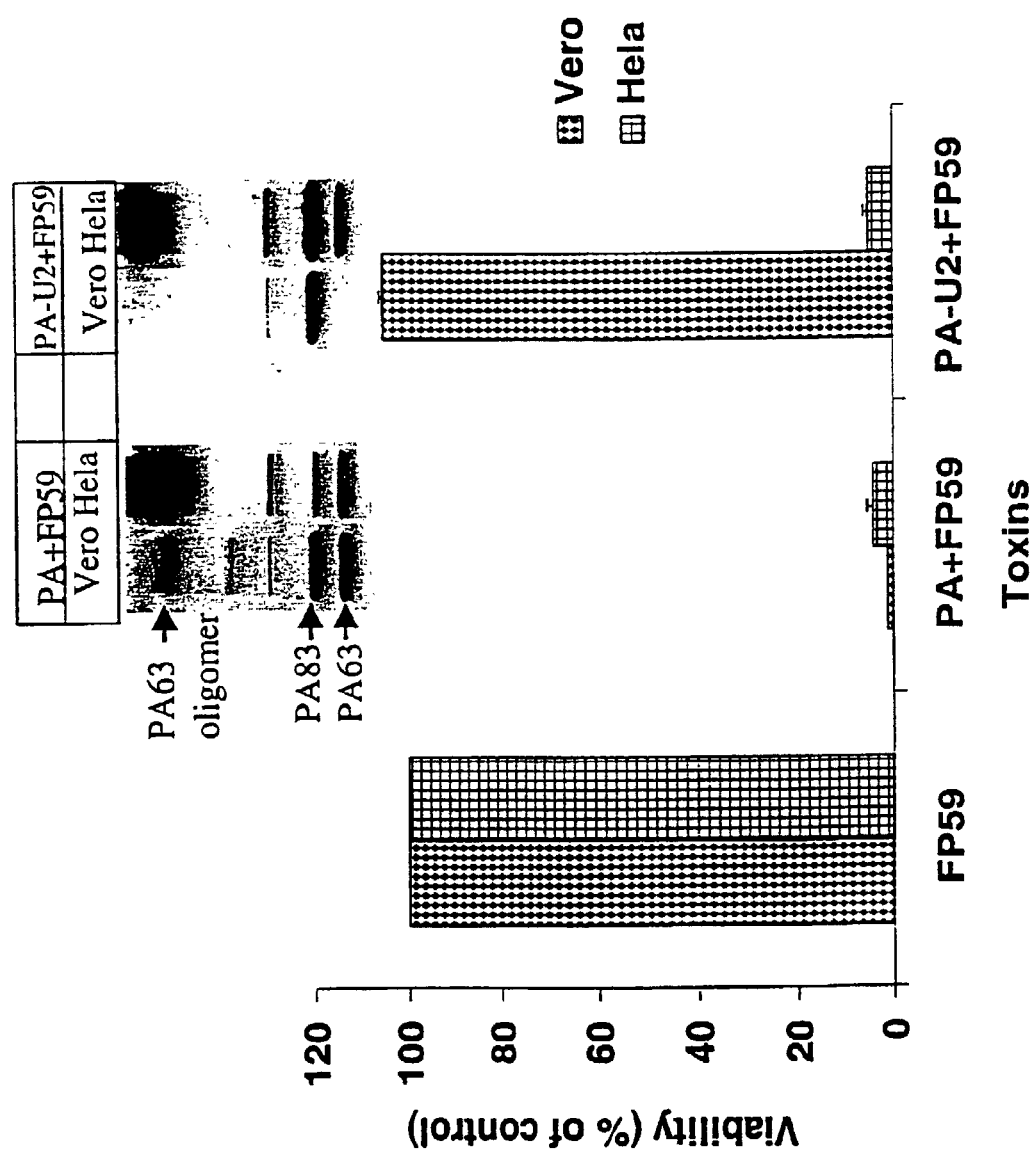

A co-culture model was designed to mimic in vivo conditions, to test whether PA-U2 can selectively kill Hela cells but not the bystander cells. Vero and Hela cells were cultured in separate compartments of 8-chamber slides. When the cells reached confluence, the chamber partitions were removed and the slides were put into culture dishes with serum-free medium containing 100 ng/ml of pro-uPA and 1 µg/ml of glu-plasminogen so that all cells on the slide were bathed in the same medium. PA and PA-U2 (each at 300 ng/ml) plus FP59 (50 ng/ml), or FP59 alone were added to the culture dishes and incubated for 48 h before measuring viability. The results showed that PA was processed to active PA63 by and killed both cells, whereas PA-U2 was processed to active PA63 by and killed only Hela cells, while not affecting the uPAR non-expressing Vero cells (FIG. 16. inset). These results showed that PA-U2 is not activated in the tissue culture medium by uPAR unbound uPA, nor do PA proteins proteolytically activated on the surface of one cell dissociate and rebind on other cells. Activate uPA in the culture supernatant would have led to killing of the Vero cells, because FIG. 12b showed that PA-U cleaved in solution became cytotoxic.

PA-U4 was Toxic to tPA Expressing Cells While PA-U2 and PA-U3 are not

Figure 17:
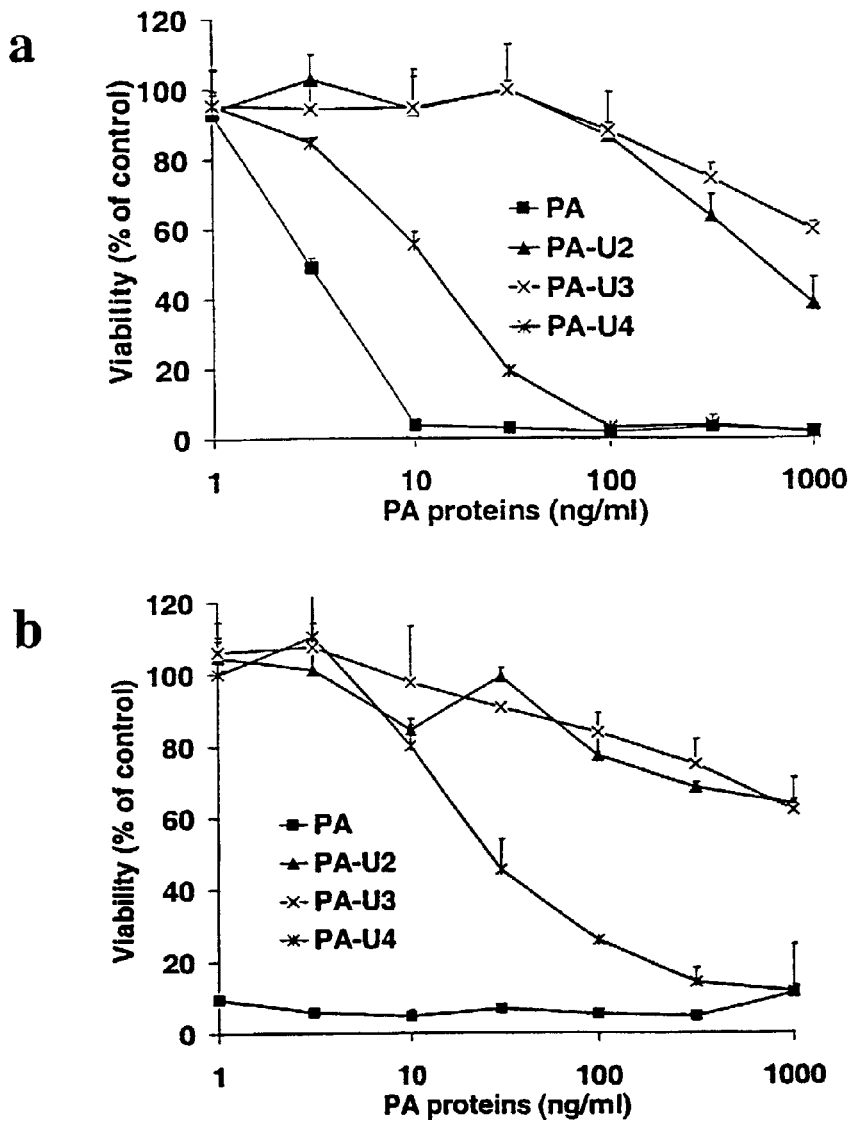

FIG. 9 showed PA-U4 is a good substrate of tPA among these mutated PA proteins and expected to be toxic to tPA expressing cells. To test this hypothesis, cytotoxicity assay was performed on two tPA expressing cells: human melanoma Bowes, and human primary vascular endothelial cells (HUVEC). The expression of tPA by these cells was evidenced by Western blotting analysis of the culture supernatants by using a polyclonal antibody against human tPA (data not shown). The cells were cultured to 50% confluence, then cytotoxicity assay were done in serum-free DMEM not containing pro-uPA and glu-plasminogen. Different concentrations (from 0 to 1000 ng/ml) of PA, PA-U2, PA-U3, and PA-U4 combined with FP59 (50 ng/ml) were incubated with cells for 12 h, and viability was measured after 48 h. The $EC_{50}$ values for the PA proteins were summarized in Table 5. PA-U4 was toxic to the two tPA expressing cells, while PA-U2 and PA-U3 showed a very low toxicity to them (FIG. 17a, b and Table 5). These and the above results clearly showed that uPA and tPA susceptibility differentiate among these mutated PA proteins. PA-U2 and PA-U3 which specifically target tumor cell surface-associated plasminogen activation system may be very useful for tumor therapy. While PA-U4 which could be activated by tPA may be applied for some neurosystem tumors which usually overexpress tPA.

Discussion

Increasing evidence has been accumulated that the components of the urokinase plasminogen activation system are involved in tumor cell proliferation, invasion, and metastasis since 1976 when it was discovered that uPA was produced and released from cancer cells (Schmitt, M., et al., *Thromb. Haemost.*, 78:285-296 (1997)). Recent data suggested that invasion factors may also serve as targets for new treatments to prevent cancer invasion and metastasis (Schmitt, M., et al., *Thromb. Haemost.*, 78:285-296 (1997)). Various different approaches to interfere with the expression or the activity of uPA, uPAR, and PAI-1 at gene or protein level were successfully tested in vitro or in mice including antisense oligonucleotides, antibodies, inhibitors, and recombinant or synthetic uPA and uPAR analogues (Schmitt, M., et al., *Thromb. Haemost.*, 78:285-296 (1997)). However, it is expected that these approaches should only slow the growth of tumors, without having a direct cytotoxic action that could eradicate the malignant cells. The present study is the first to exploit the tumor cell surface associated plasminogen system to achieve cell-type selective targeting of cytotoxic bacterial toxin fusion proteins. In this study, mutated anthrax toxin protective antigen (PA) proteins, PA-U2, PA-U3, and PA-U4, were constructed in which the furin recognition site is replaced by susceptible sequences cleaved by uPA (PA-U2 and PA-U3) or tPA (PA-U4) more efficiently than control peptides containing the physiological target sequence present in plasminogen. More interestingly is that the susceptibility toward uPA and tPA differentiated among these mutated PA proteins, i.e., PA-U2 and PA-U3 were mainly activated by uPA, while PA-U4 was mainly activated by tPA. Thus, when combined with FP59, a recombinant fusion toxin derived from anthrax lethal factor and *Pseudomonas* exotoxin A, PA-U2 and PA-U3 selectively killed uPAR-overexpressing tumor cells in the present of pro-uPA, and meanwhile showed very low toxicity to tPA expressing cells such as vascular endothelial cells. Because tPA is secreted as an active enzyme mainly by vascular endothelial cells in vivo (Mann, K., et al., *Annu. Rev. Biochem.*, 57:915-956 (1988)), the cytotoxicity differentiation among these mutated PA proteins to uPA and tPA expression cells is so important to avoid the damage to the vascular endothelial cells when PA-U2 and PA-U3 are used in vivo.

The following lines of evidence clearly demonstrate that the proteolytic activation of these uPA-activated mutated PA proteins occurred on the tumor cell surface that was dependent upon the activity of tumor cell surface associated plasminogen activation system: 1. Pro-uPA could only bind and thereby proteolytically activated on uPAR-expressing tumor cell surface but not on uPAR non-expressing Vero cells; 2. PA-U2 could only be proteolytically processed to the active form PA63 on uPAR-expressing cells (such as Hela cells) but not on uPAR non-expressing Vero cells, and this processing could be completely inhibited by uPA specific inhibitor PAI-1; 3. The toxicity of PA-U2 to the tumor cells was eliminated by uPAR specific blocking reagent ATF, UPAR blocking antibody R3, and PAI-1, demonstrating the activation of PA-U2 was entirely dependent upon the activation of pro-uPA on tumor cell surface; 4. Cytotoxicity assays in a co-culture model, in which the cells were equally accessible to the toxins in the supernatant, showed that PA-U2 killed only uPAR-overexpressing Hela cells and not the bystander Vero cells, demonstrating that activation of uPA-activated mutated PA proteins occurred principally on cell surfaces, because the active form of PA proteins in solution could also kill the Vero cells.

PA proteins bind to cells rapidly and with high affinity (Kd approx. 1 nM), therefore, even at low PA concentrations, PA receptors will be highly occupied. As a result, if there were any PA which became activated in the supernatant or dissociated from a cell after cleavage would be unable to locate a free receptor by which to bind to cells and internalize FP59.

Thus, the cytotoxicity of these cytotoxins was directed selectively to the uPAR-overexpressing tumor cells. PA-U4, which could be activated by tPA, can be applied for intratumoral therapy of some unresectable neurosystem tumors which usually overexpress tPA.

Tumor-cell selective cytotoxins have been created by replacing the receptor-recognition domains of bacterial and plant protein toxins with cytokines, growth factors, and antibodies (Kreitman, R. J., *Curr. Opin. Immunol.*, 11:570-578 (1999)). The protein toxins used contain an enzymatic domain that acts in the cytosol to inhibit protein synthesis and a domain which achieves translocation of this catalyst from a vesicular compartment to the cytosol, as well as the cell-targeting domain that is replaced or altered so as to achieve tumor cell specificity. Certain of these "immunotoxins" derived from diphtheria toxin, *Pseudomonas* exotoxin A, and ricin have shown efficacy and have been approved for clinical use. However, a recurrent problem with these materials is that therapeutic doses typically damage other tissues and cells (Frankel, A. E., et al., *Semin. Cancer Biol.*, 6:307-317 (1995)). This is not surprising because very few of the tumor cell surface receptors or antigens that are targeted are totally absent from normal tissue. Therefore, even in the best cases, some toxin uptake will occur in normal bystander cells. Because these toxins act catalytically, even a small amount of internalized toxin can seriously damage normal tissue. Even a single molecule delivered to the cytosol can kill a cell (Yamaizumi, M., et al., *Cell*, 15:245-250 (1978)). Previous efforts to develop anthrax toxin fusion proteins as therapeutic agents have focused on modification of domain 4, the receptor-binding domain of PA. Work is ongoing to create cell-type specific cytotoxic agents by modifying or replacing domain 4 to direct PA to alternate receptors (Varughese, M., et al., *Mol. Med.*, 4:87-95 (1998); Varughese, M., et al., *Infect. Immun.*, 67:1860-1865 (1999). This work follows the example of the development of immunotoxins from other protein toxins, as cited earlier (Kreitman, R. J., *Curr. Opin. Immunol.*, 11:570-578 (1999)). We suggest that combining two conceptually distinct targeting strategies in a single PA protein will yield agents having higher therapeutic indices. A protein that is both retargeted to a tumor cell surface protein and dependent on cell surface plasminogen activation system for activation may achieve therapeutic effects while being free of the side effects observed with many of the existing immunotoxins.

TABLE 3

PA proteins generated in this study

| Designation | Sequence at the "furin loop" | | SEQ ID NO: | $K_{cat}/Km^1$ | | uPA:tPA selectivity[1] | Protease expected to cleave |
|---|---|---|---|---|---|---|---|
| | | | | uPA | tPA | | |
| PA | NS RKKR↑ | STSAGPTV | 23 | | | | Furin |
| PA-U1 | NSPCPGR↑ VVGG | STSAGPTV | 24 | 0.88 | 0.29 | 3 | uPA/tPA (weakly) |
| PA-U2 | NSPGSGR↑ SA | STSAGPTV | 25 | 1200 | 60 | 20 | uPA |
| PA-U3 | NSPGSGK↑ SA | STSAGPTV | 26 | 193 | 1.6 | 121 | uPA |
| PA-U4 | NSPQRGR↑ SA | STSAGPTV | 27 | 7.3 | 670 | 0.005 | tPA |
| PA-U7 | NSPGG | STSAGPTV | 28 | | | | None |

[1]Data was cited from Ke, S. H., et al., J. Biol. Chem., 272:20456-20462 (1997) which was obtained from the studies on the peptides underlined in column 2.

TABLE 4

| Toxicities ($EC_{50}$ in μg/ml) of PA proteins to various cells | | | | | |
|---|---|---|---|---|---|
| Cell line | Cell type | PA | PA-U2 | PA-U3 | PA-U4 |
| Hela | Human cervix adenocarcinoma cell line | 12 | 14 | 30 | 200 |
| A2058 | Human melanoma cell line | 10 | 13 | 18 | 50 |
| Bowes | Human melanoma cell line | 7 | 8 | 15 | 50 |
| Vero | Monkey kidney normal epithelial cell line | 15 | >1000 | >1000 | >1000 |

$EC_{50}$ is the concentration of toxin required to kill half of the cells. $EC_{50}$ values are interpolated from FIGS. 11 and 12.

TABLE 5

| Toxicities ($EC_{50}$ in ng/ml) of PA proteins to tPA expressing cells | | | | | |
|---|---|---|---|---|---|
| Cell line | Cell type | PA | PA-U2 | PA-U3 | PA-U4 |
| HUVEC | Human primary vascular endotheial cells | <1 | >1000 | >1000 | 25 |
| Bowes | Human melanoma cell line | 3 | 600 | >1000 | 12 |

$EC_{50}$ is the concentration of toxin required to kill half of the cells. $EC_{50}$ values are interpolated from FIG. 17.

What is claimed is:

1. A method of targeting a compound to a carcinoma or fibrosarcoma cell over-expressing uPA and uPAR, the method comprising the steps of:
   (i) administering to the carcinoma or fibrosarcoma cell a mutant protective antigen protein comprising a uPA-recognized cleavage site in place of the native protective antigen furin-recognized cleavage site, wherein the uPA-recognized cleavage site is PGSGRSA (SEQ ID NO: 5), and wherein the mutant protective antigen is cleaved by uPA; and
   (ii) administering to the carcinoma or fibrosarcoma cell a compound comprising a lethal factor polypeptide comprising a protective antigen binding site; wherein the lethal factor polypeptide binds to cleaved protective antigen and is translocated into the carcinoma or fibrosarcoma cell, thereby delivering the compound to the carcinoma or fibrosarcoma cell.

2. The method of claim 1, wherein the carcinoma is lung.

3. The method of claim 1, wherein the lethal factor polypeptide is native lethal factor.

4. The method of claim 1, wherein the compound is native lethal factor.

5. The method of claim 1, wherein the lethal factor polypeptide is linked to a heterologous compound.

6. The method of claim 5, wherein the compound is shiga toxin, A chain of diphtheria toxin, or *Pseudomonas* exotoxin A.

7. The method of claim 5, wherein the heterologous compound is recombinantly linked to lethal factor.

8. The method of claim 1, wherein the compound is a diagnostic or a therapeutic agent.

9. The method of claim 1, wherein the cell is a human cell.

10. The method of claim 1, wherein the mutant protective antigen protein is a fusion protein comprising a heterologous receptor binding domain.

11. The method of claim 10, wherein the heterologous receptor binding domain is selected from the group consisting of a single chain antibody and a growth factor.

12. The method of claim 1, wherein the lethal factor polypeptide comprises amino acids 1-254 of native lethal factor.

13. The method of claim 12, wherein the lethal factor polypeptide is linked to a heterologous compound.

14. The method of claim 13, wherein the heterologous compound is the ADP-ribosylation domain of *Pseudomonas* exotoxin A.

15. The method of claim 14, wherein the lethal factor polypeptide is recombinantly linked to the ADP-ribosylation domain of *Pseudomonas* exotoxin A.

16. The method of claim 14, wherein the lethal factor polypeptide is covalently linked to the ADP-ribosylation domain of *Pseudomonas* exotoxin A by a chemical bond.

17. The method of claim 5, wherein the compound is covalently linked to lethal factor via a chemical bond.

* * * * *